US012616534B2

(12) United States Patent
Moll et al.

(10) Patent No.: US 12,616,534 B2
(45) Date of Patent: May 5, 2026

(54) SURGICAL SYSTEM WITH CONFIGURABLE MECHANICAL ARMS STOWABLE BENEATH A SURGICAL BED

(71) Applicant: Auris Health, Inc., Redwood City, CA (US)

(72) Inventors: Frederic H. Moll, San Francisco, CA (US); Alan Lau Yu, Union City, CA (US)

(73) Assignee: Auris Health, Inc., Santa Clara, CA (US)

( * ) Notice: Subject to any disclaimer, the term of this patent is extended or adjusted under 35 U.S.C. 154(b) by 0 days.

(21) Appl. No.: 18/653,622

(22) Filed: May 2, 2024

(65) Prior Publication Data

US 2024/0277429 A1 Aug. 22, 2024

Related U.S. Application Data

(63) Continuation of application No. 16/914,873, filed on Jun. 29, 2020, now Pat. No. 12,193,769, which is a
(Continued)

(51) Int. Cl.
*A61B 34/30* (2016.01)
*A61B 1/00* (2006.01)
(Continued)

(52) U.S. Cl.
CPC .......... *A61B 34/30* (2016.02); *A61B 1/00149* (2013.01); *A61B 34/00* (2016.02);
(Continued)

(58) Field of Classification Search
CPC ......... A61B 34/00; A61B 34/20; A61B 34/30; A61B 50/10; A61B 1/00149;
(Continued)

(56) References Cited

U.S. PATENT DOCUMENTS

| | | | |
|---|---|---|---|
| 3,997,926 A | 12/1976 | England | |
| 4,878,494 A | 11/1989 | Phillips et al. | |

(Continued)

FOREIGN PATENT DOCUMENTS

| | | |
|---|---|---|
| CN | 202314134 U | 7/2012 |
| GB | 810956 A | 3/1959 |
| WO | 2010/068005 A2 | 6/2010 |

OTHER PUBLICATIONS

Darwiche, Fadi, et al. "Operative technique and early experience for robotic-assisted laparoscopic nephroureterectomy (RALNU) using da Vinci Xi." *Springerplus* 4 (2015): 1-5.
(Continued)

*Primary Examiner* — David R Hare
(74) *Attorney, Agent, or Firm* — FBT Gibbons LLP

(57) ABSTRACT

A robotic surgical system comprises a horizontal platform to support a patient, a rail positioned about the horizontal platform, a carriage operatively coupled to and configured to translate along the rail, and a robotic arm operatively coupled to the carriage and translated about the patient by the rail. The robotic arm is configured to operate on the patient in a variety of positions provided by the translating carriage. The rail provides a rounded path for the carriage, such as a U-shaped path. The U-shaped path may comprise a first leg and a second leg, the first leg longer than the second leg. Furthermore, the system may comprise a plurality of carriages operatively coupled to the rail and a plurality of robotic arms. Also, the system may further comprise a central base which the horizontal platform can articulate relative to, such as by translating horizontally or vertically, rotating, or titling.

20 Claims, 20 Drawing Sheets

504 505 506

502

503

507

508

500

501

Related U.S. Application Data continuation of application No. 16/195,206, filed on Nov. 19, 2018, now Pat. No. 10,702,348, which is a continuation of application No. 15/094,179, filed on Apr. 8, 2016, now Pat. No. 10,159,533.

(60) Provisional application No. 62/145,418, filed on Apr. 9, 2015.

(51) Int. Cl.

| | |
|---|---|
| A61B 1/267 | (2006.01) |
| A61B 1/273 | (2006.01) |
| A61B 1/303 | (2006.01) |
| A61B 1/307 | (2006.01) |
| A61B 1/31 | (2006.01) |
| A61B 1/313 | (2006.01) |
| A61B 34/00 | (2016.01) |
| A61B 34/20 | (2016.01) |
| A61B 50/10 | (2016.01) |
| A61B 90/50 | (2016.01) |
| A61B 90/57 | (2016.01) |
| A61G 13/04 | (2006.01) |
| A61G 13/06 | (2006.01) |
| A61G 13/10 | (2006.01) |

(52) U.S. Cl.

CPC .............. *A61B 34/20* (2016.02); *A61B 50/10* (2016.02); *A61B 90/50* (2016.02); *A61G 13/04* (2013.01); *A61G 13/06* (2013.01); *A61G 13/10* (2013.01); *A61B 1/2676* (2013.01); *A61B 1/2736* (2013.01); *A61B 1/303* (2013.01); *A61B 1/307* (2013.01); *A61B 1/31* (2013.01); *A61B 1/3132* (2013.01); *A61B 2034/304* (2016.02); *A61B 2090/571* (2016.02); *A61G 13/101* (2013.01)

(58) Field of Classification Search

CPC ..... A61B 1/2676; A61B 1/2736; A61B 1/303; A61B 1/307; A61B 1/31; A61B 1/3132; A61B 2034/304; A61B 2090/571; A61G 13/04; A61G 13/06; A61G 13/10; A61G 13/101

USPC ............................................... 606/130; 5/658

See application file for complete search history.

(56) References Cited

U.S. PATENT DOCUMENTS

| | | | |
|---|---|---|---|
| 5,013,018 A | 5/1991 | Sicek | |
| 5,160,106 A | 11/1992 | Monick | |
| 5,199,417 A | 4/1993 | Muller et al. | |
| 5,259,365 A | 11/1993 | Nishikori | |
| 5,405,604 A | 4/1995 | Has et al. | |
| 5,555,897 A | 9/1996 | Lathrop, Jr. et al. | |
| 5,571,072 A | 11/1996 | Kronner | |
| 5,597,146 A | 1/1997 | Putman | |
| 5,762,458 A | 6/1998 | Wang et al. | |
| 5,814,038 A | 9/1998 | Jensen et al. | |
| 5,855,583 A | 1/1999 | Wang et al. | |
| 5,876,325 A | 3/1999 | Mizuno et al. | |
| 5,926,875 A | 7/1999 | Okamoto et al. | |
| 5,944,476 A | 8/1999 | Bacchi et al. | |
| 6,170,102 B1 | 1/2001 | Kreuzer | |
| 6,202,230 B1 | 3/2001 | Borders | |
| 6,620,174 B2 | 9/2003 | Jensen et al. | |
| 6,632,170 B1 | 10/2003 | Bohanan et al. | |
| 6,640,363 B1 | 11/2003 | Pattee et al. | |
| 6,676,669 B2 | 1/2004 | Charles et al. | |
| 6,788,018 B1 | 9/2004 | Blumenkranz | |
| 6,804,581 B2 | 10/2004 | Wang | |
| 7,025,761 B2 | 4/2006 | Wang et al. | |
| 7,027,892 B2 | 4/2006 | Wang et al. | |
| 7,074,179 B2 | 7/2006 | Wang et al. | |
| 7,763,015 B2 | 7/2010 | Cooper et al. | |
| 7,789,874 B2 | 9/2010 | Yu et al. | |
| 7,850,642 B2 | 12/2010 | Moll et al. | |
| 7,963,288 B2 | 6/2011 | Rosenberg et al. | |
| 7,972,298 B2 | 7/2011 | Wallace et al. | |
| 7,974,681 B2 | 7/2011 | Wallace et al. | |
| 7,976,539 B2 | 7/2011 | Hlavka et al. | |
| 7,979,157 B2 * | 7/2011 | Anvari ................... | A61G 13/10 |
| | | | 700/251 |
| 7,996,110 B2 | 8/2011 | Lipow et al. | |
| 8,005,537 B2 | 8/2011 | Hlavka et al. | |
| 8,021,326 B2 | 9/2011 | Moll et al. | |
| 8,052,636 B2 | 11/2011 | Moll et al. | |
| 8,108,069 B2 | 1/2012 | Stahler et al. | |
| 8,142,420 B2 | 3/2012 | Schena | |
| 8,146,874 B2 | 4/2012 | Yu | |
| 8,172,747 B2 | 5/2012 | Wallace et al. | |
| 8,190,238 B2 | 5/2012 | Moll et al. | |
| 8,230,863 B2 | 7/2012 | Ravikumar et al. | |
| 8,257,303 B2 | 9/2012 | Moll et al. | |
| 8,311,626 B2 | 11/2012 | Hlavka et al. | |
| 8,343,096 B2 | 1/2013 | Kirschenman et al. | |
| 8,348,931 B2 | 1/2013 | Cooper et al. | |
| 8,394,054 B2 | 3/2013 | Wallace et al. | |
| 8,400,094 B2 | 3/2013 | Schena | |
| 8,409,136 B2 | 4/2013 | Wallace et al. | |
| 8,409,172 B2 | 4/2013 | Moll et al. | |
| 8,414,598 B2 | 4/2013 | Brock et al. | |
| 8,425,404 B2 | 4/2013 | Wilson et al. | |
| 8,469,945 B2 | 6/2013 | Schena | |
| 8,498,691 B2 | 7/2013 | Moll et al. | |
| 8,506,556 B2 | 8/2013 | Schena | |
| 8,512,353 B2 | 8/2013 | Rosielle et al. | |
| 8,515,576 B2 | 8/2013 | Lipow et al. | |
| 8,617,102 B2 | 12/2013 | Moll et al. | |
| 8,641,698 B2 | 2/2014 | Sanchez et al. | |
| 8,652,030 B2 | 2/2014 | Matsuura et al. | |
| 8,801,661 B2 | 8/2014 | Moll et al. | |
| 8,897,920 B2 | 11/2014 | Wang et al. | |
| 8,911,429 B2 | 12/2014 | Olds et al. | |
| 8,926,603 B2 | 1/2015 | Hlavka et al. | |
| 8,960,622 B2 | 2/2015 | von Pechmann et al. | |
| 8,968,333 B2 | 3/2015 | Yu et al. | |
| 8,974,408 B2 | 3/2015 | Wallace et al. | |
| 9,023,060 B2 | 5/2015 | Cooper et al. | |
| 9,078,686 B2 | 7/2015 | Schena | |
| 9,119,653 B2 | 9/2015 | Girbau et al. | |
| 9,119,655 B2 | 9/2015 | Bowling et al. | |
| 9,259,281 B2 | 2/2016 | Griffiths et al. | |
| 9,314,306 B2 | 4/2016 | Yu | |
| 9,326,822 B2 | 5/2016 | Lewis et al. | |
| 9,358,076 B2 | 6/2016 | Moll et al. | |
| 9,408,669 B2 | 8/2016 | Kokish et al. | |
| 9,452,018 B2 | 9/2016 | Yu | |
| 9,457,168 B2 | 10/2016 | Moll et al. | |
| 9,504,604 B2 | 11/2016 | Alvarez | |
| 9,554,865 B2 | 1/2017 | Olds et al. | |
| 9,561,083 B2 | 2/2017 | Yu et al. | |
| 9,566,201 B2 | 2/2017 | Yu | |
| 9,579,088 B2 | 2/2017 | Farritor et al. | |
| 9,615,889 B2 | 4/2017 | Jensen | |
| 9,622,825 B2 | 4/2017 | Phee et al. | |
| 9,622,827 B2 | 4/2017 | Yu et al. | |
| 9,629,682 B2 | 4/2017 | Wallace et al. | |
| 9,636,184 B2 | 5/2017 | Lee et al. | |
| 9,668,768 B2 | 6/2017 | Piron et al. | |
| 9,713,499 B2 | 7/2017 | Bar et al. | |
| 9,713,509 B2 | 7/2017 | Schuh et al. | |
| 9,717,563 B2 | 8/2017 | Tognaccini | |
| 9,727,963 B2 | 8/2017 | Mintz et al. | |
| 9,737,371 B2 | 8/2017 | Romo et al. | |
| 9,737,373 B2 | 8/2017 | Schuh | |
| 9,744,335 B2 | 8/2017 | Jiang | |
| 9,763,741 B2 | 9/2017 | Alvarez et al. | |
| 9,788,910 B2 | 10/2017 | Schuh | |
| 9,795,454 B2 | 10/2017 | Seeber et al. | |
| 9,814,640 B1 | 11/2017 | Khaligh | |

(56) References Cited

U.S. PATENT DOCUMENTS

| | | | |
|---|---|---|---|
| 9,820,819 B2 | 11/2017 | Olson | |
| 9,844,412 B2 | 12/2017 | Bogusky et al. | |
| 9,850,924 B2 | 12/2017 | Vogtherr et al. | |
| 9,867,635 B2 | 1/2018 | Alvarez et al. | |
| 9,907,458 B2 | 3/2018 | Schena | |
| 9,918,681 B2 | 3/2018 | Wallace et al. | |
| 9,931,025 B1 | 4/2018 | Graetzel et al. | |
| 9,949,749 B2 | 4/2018 | Noonan et al. | |
| 9,955,986 B2 | 5/2018 | Shah | |
| 9,962,228 B2 | 5/2018 | Schuh et al. | |
| 9,980,785 B2 | 5/2018 | Schuh | |
| 9,993,313 B2 | 6/2018 | Schuh et al. | |
| 9,999,476 B2 | 6/2018 | Griffiths | |
| 10,016,900 B1 | 7/2018 | Meyer et al. | |
| 10,022,192 B1 | 7/2018 | Ummalaneni | |
| 10,080,576 B2 | 9/2018 | Romo et al. | |
| 10,136,959 B2 | 11/2018 | Mintz et al. | |
| 10,145,747 B1 | 12/2018 | Lin et al. | |
| 10,149,720 B2 | 12/2018 | Romo | |
| 10,159,532 B1 | 12/2018 | Ummalaneni et al. | |
| 10,159,533 B2 | 12/2018 | Moll et al. | |
| 10,169,875 B2 | 1/2019 | Mintz et al. | |
| 10,219,874 B2 | 3/2019 | Yu et al. | |
| 10,231,793 B2 | 3/2019 | Romo | |
| 10,231,867 B2 | 3/2019 | Alvarez et al. | |
| 10,244,926 B2 | 4/2019 | Noonan et al. | |
| 10,285,574 B2 | 5/2019 | Landey et al. | |
| 10,299,870 B2 | 5/2019 | Connolly et al. | |
| 10,314,463 B2 | 6/2019 | Agrawal et al. | |
| 10,350,390 B2 | 7/2019 | Moll et al. | |
| 10,368,951 B2 | 8/2019 | Moll et al. | |
| 10,376,672 B2 | 8/2019 | Yu | |
| 10,383,765 B2 | 8/2019 | Alvarez et al. | |
| 10,398,518 B2 | 9/2019 | Yu et al. | |
| 10,405,939 B2 | 9/2019 | Romo et al. | |
| 10,405,940 B2 | 9/2019 | Romo | |
| 10,426,559 B2 | 10/2019 | Graetzel et al. | |
| 10,426,661 B2 | 10/2019 | Kintz | |
| 10,434,660 B2 | 10/2019 | Meyer | |
| 10,464,209 B2 | 11/2019 | Ho et al. | |
| 10,470,830 B2 | 11/2019 | Hill | |
| 10,482,599 B2 | 11/2019 | Mintz et al. | |
| 10,493,241 B2 | 12/2019 | Jiang | |
| 10,500,001 B2 | 12/2019 | Yu et al. | |
| 10,517,692 B2 | 12/2019 | Eyre et al. | |
| 10,524,866 B2 | 1/2020 | Srinivasan | |
| 10,539,478 B2 | 1/2020 | Lin | |
| 10,543,047 B2 | 1/2020 | Yu | |
| 10,543,048 B2 | 1/2020 | Noonan et al. | |
| 10,555,778 B2 | 2/2020 | Ummalaneni et al. | |
| 10,556,092 B2 | 2/2020 | Yu et al. | |
| 10,631,949 B2 | 4/2020 | Schuh et al. | |
| 10,639,108 B2 | 5/2020 | Romo et al. | |
| 10,639,109 B2 | 5/2020 | Bovay et al. | |
| 10,639,114 B2 | 5/2020 | Schuh | |
| 10,667,871 B2 | 6/2020 | Romo et al. | |
| 10,667,875 B2 | 6/2020 | DeFonzo | |
| 10,682,189 B2 | 6/2020 | Schuh et al. | |
| 10,702,348 B2 * | 7/2020 | Moll | A61G 13/06 |
| 10,716,461 B2 | 7/2020 | Jenkins | |
| 10,743,751 B2 | 8/2020 | Landey et al. | |
| 10,744,035 B2 | 8/2020 | Alvarez et al. | |
| 10,821,046 B2 | 11/2020 | Hares et al. | |
| 12,023,119 B2 | 7/2024 | Mao et al. | |
| 12,193,769 B2 * | 1/2025 | Moll | A61G 13/04 |
| 2002/0082612 A1 | 6/2002 | Moll et al. | |
| 2002/0162926 A1 | 11/2002 | Nguyen | |
| 2002/0165524 A1 | 11/2002 | Sanchez et al. | |
| 2002/0170116 A1 | 11/2002 | Borders | |
| 2003/0181809 A1 | 9/2003 | Hall et al. | |
| 2003/0191455 A1 | 10/2003 | Sanchez et al. | |
| 2004/0243147 A1 | 12/2004 | Lipow | |
| 2004/0261179 A1 | 12/2004 | Blumenkranz | |
| 2005/0222554 A1 | 10/2005 | Wallace et al. | |
| 2006/0069383 A1 | 3/2006 | Bogaerts | |
| 2006/0149418 A1 * | 7/2006 | Anvari | A61B 34/74 |
| | | | 700/245 |
| 2006/0161136 A1 | 7/2006 | Anderson et al. | |
| 2006/0178556 A1 | 8/2006 | Hasser et al. | |
| 2006/0200026 A1 | 9/2006 | Wallace et al. | |
| 2007/0137371 A1 | 6/2007 | Devengenzo et al. | |
| 2007/0293734 A1 | 12/2007 | Coste-Maniere et al. | |
| 2008/0027464 A1 | 1/2008 | Moll et al. | |
| 2008/0039867 A1 | 2/2008 | Feussner et al. | |
| 2008/0082109 A1 | 4/2008 | Moll et al. | |
| 2008/0147089 A1 | 6/2008 | Loh | |
| 2008/0167750 A1 | 7/2008 | Stahler | |
| 2008/0195081 A1 | 8/2008 | Moll et al. | |
| 2008/0218770 A1 | 9/2008 | Moll et al. | |
| 2008/0245946 A1 | 10/2008 | Yu | |
| 2009/0005768 A1 | 1/2009 | Sharareh | |
| 2009/0036900 A1 | 2/2009 | Moll | |
| 2009/0041565 A1 | 2/2009 | Rodriguez Y Baena | |
| 2009/0048611 A1 | 2/2009 | Funda | |
| 2009/0062602 A1 | 3/2009 | Rosenberg et al. | |
| 2009/0163928 A1 | 6/2009 | Schena | |
| 2009/0171332 A1 | 7/2009 | Bonneau | |
| 2009/0240371 A1 | 9/2009 | Wang et al. | |
| 2009/0326318 A1 | 12/2009 | Tognaccini | |
| 2010/0100045 A1 | 4/2010 | Pravongviengkham et al. | |
| 2010/0185211 A1 | 7/2010 | Herman | |
| 2010/0204713 A1 | 8/2010 | Ruiz | |
| 2010/0234857 A1 | 9/2010 | Itkowitz et al. | |
| 2010/0286712 A1 * | 11/2010 | Won | A61B 34/30 |
| | | | 606/130 |
| 2011/0028894 A1 | 2/2011 | Foley et al. | |
| 2011/0187875 A1 | 8/2011 | Sanchez et al. | |
| 2011/0238083 A1 | 9/2011 | Moll et al. | |
| 2011/0257786 A1 | 10/2011 | Caron | |
| 2011/0270273 A1 | 11/2011 | Moll et al. | |
| 2011/0277775 A1 | 11/2011 | Holop et al. | |
| 2011/0282359 A1 | 11/2011 | Duval | |
| 2012/0078053 A1 | 3/2012 | Phee et al. | |
| 2012/0191079 A1 | 7/2012 | Moll et al. | |
| 2012/0191083 A1 | 7/2012 | Moll et al. | |
| 2012/0191086 A1 | 7/2012 | Moll et al. | |
| 2012/0241576 A1 | 9/2012 | Yu | |
| 2012/0253332 A1 | 10/2012 | Moll | |
| 2012/0266379 A1 | 10/2012 | Hushek | |
| 2012/0277764 A1 | 11/2012 | Cooper et al. | |
| 2012/0283747 A1 | 11/2012 | Popovic | |
| 2012/0296161 A1 | 11/2012 | Wallace et al. | |
| 2012/0302869 A1 | 11/2012 | Koyrakh | |
| 2013/0041219 A1 | 2/2013 | Hasegawa et al. | |
| 2013/0053866 A1 | 2/2013 | Leung et al. | |
| 2013/0096576 A1 | 4/2013 | Cooper | |
| 2013/0131695 A1 | 5/2013 | Scarfogliero et al. | |
| 2013/0190741 A1 | 7/2013 | Moll et al. | |
| 2013/0255425 A1 | 10/2013 | Schena | |
| 2013/0310639 A1 | 11/2013 | Omori | |
| 2013/0338679 A1 | 12/2013 | Rosielle et al. | |
| 2014/0018960 A1 | 1/2014 | Itkowitz | |
| 2014/0051049 A1 | 2/2014 | Jarc | |
| 2014/0051987 A1 | 2/2014 | Kowshik et al. | |
| 2014/0142591 A1 | 5/2014 | Alvarez et al. | |
| 2014/0180309 A1 | 6/2014 | Seeber et al. | |
| 2014/0188132 A1 | 7/2014 | Kang | |
| 2014/0243801 A1 | 8/2014 | Fanelli et al. | |
| 2014/0249546 A1 | 9/2014 | Shvartsberg et al. | |
| 2014/0276647 A1 | 9/2014 | Yu | |
| 2014/0276935 A1 | 9/2014 | Yu | |
| 2014/0277333 A1 | 9/2014 | Lewis et al. | |
| 2014/0277334 A1 | 9/2014 | Yu et al. | |
| 2014/0357984 A1 | 12/2014 | Wallace et al. | |
| 2015/0025549 A1 | 1/2015 | Kilroy et al. | |
| 2015/0038981 A1 | 2/2015 | Kilroy et al. | |
| 2015/0045675 A1 | 2/2015 | Chernomorsky | |
| 2015/0119637 A1 | 4/2015 | Alvarez et al. | |
| 2015/0239082 A1 | 8/2015 | Krouglicof et al. | |
| 2015/0297299 A1 | 10/2015 | Yeung | |
| 2015/0305650 A1 | 10/2015 | Hunter | |
| 2015/0335389 A1 | 11/2015 | Greenberg | |
| 2016/0001038 A1 | 1/2016 | Romo et al. | |
| 2016/0100896 A1 | 4/2016 | Yu | |

(56) References Cited

U.S. PATENT DOCUMENTS

| | | | |
|---|---|---|---|
| 2016/0157942 A1* | 6/2016 | Gombert | A61B 34/30 |
| | | | 606/130 |
| 2016/0220324 A1 | 8/2016 | Tesar | |
| 2016/0270865 A1 | 9/2016 | Landey et al. | |
| 2016/0287279 A1 | 10/2016 | Bovay et al. | |
| 2016/0302871 A1 | 10/2016 | Gregerson et al. | |
| 2016/0338785 A1 | 11/2016 | Kokish et al. | |
| 2016/0346052 A1 | 12/2016 | Rosielle et al. | |
| 2016/0374771 A1 | 12/2016 | Mirbagheri et al. | |
| 2017/0007337 A1 | 1/2017 | Dan | |
| 2017/0007343 A1 | 1/2017 | Yu | |
| 2017/0045807 A1 | 2/2017 | Ye | |
| 2017/0071456 A1 | 3/2017 | Ratnakar | |
| 2017/0071692 A1 | 3/2017 | Taylor et al. | |
| 2017/0071693 A1 | 3/2017 | Taylor et al. | |
| 2017/0135710 A1 | 5/2017 | Hasegawa et al. | |
| 2017/0135771 A1 | 5/2017 | Auld et al. | |
| 2017/0143442 A1 | 5/2017 | Tesar | |
| 2017/0189118 A1 | 7/2017 | Chopra | |
| 2017/0189131 A1 | 7/2017 | Weir | |
| 2017/0202627 A1 | 7/2017 | Sramek et al. | |
| 2017/0209073 A1 | 7/2017 | Sramek et al. | |
| 2017/0209217 A1 | 7/2017 | Jensen | |
| 2017/0215976 A1 | 8/2017 | Nowlin et al. | |
| 2017/0215978 A1 | 8/2017 | Wallace et al. | |
| 2017/0290631 A1 | 10/2017 | Lee et al. | |
| 2017/0304021 A1 | 10/2017 | Hathaway | |
| 2017/0325906 A1 | 11/2017 | Piecuch et al. | |
| 2017/0340353 A1 | 11/2017 | Ahluwalia et al. | |
| 2018/0025666 A1 | 1/2018 | Ho et al. | |
| 2018/0065252 A1 | 3/2018 | Tabandeh | |
| 2018/0078439 A1* | 3/2018 | Cagle | A61B 34/70 |
| 2018/0078440 A1 | 3/2018 | Koenig et al. | |
| 2018/0079090 A1 | 3/2018 | Koenig et al. | |
| 2018/0098817 A1 | 4/2018 | Nichogi et al. | |
| 2018/0116758 A1 | 5/2018 | Schlosser | |
| 2018/0177470 A1 | 6/2018 | Suga | |
| 2018/0214011 A1 | 8/2018 | Graetzel et al. | |
| 2018/0221038 A1 | 8/2018 | Noonan et al. | |
| 2018/0221039 A1 | 8/2018 | Shah | |
| 2018/0271616 A1 | 9/2018 | Schuh et al. | |
| 2018/0279852 A1 | 10/2018 | Rafii-Tari et al. | |
| 2018/0280660 A1 | 10/2018 | Landey et al. | |
| 2018/0289431 A1 | 10/2018 | Draper et al. | |
| 2018/0289445 A1 | 10/2018 | Krinninger et al. | |
| 2018/0296285 A1 | 10/2018 | Simi et al. | |
| 2018/0325499 A1 | 11/2018 | Landey et al. | |
| 2018/0338799 A1 | 11/2018 | Hladio et al. | |
| 2018/0360435 A1 | 12/2018 | Romo | |
| 2018/0368920 A1 | 12/2018 | Ummalaneni | |
| 2018/0369035 A1 | 12/2018 | Bhimavarapu et al. | |
| 2019/0000559 A1 | 1/2019 | Berman et al. | |
| 2019/0000560 A1 | 1/2019 | Berman et al. | |
| 2019/0000576 A1 | 1/2019 | Mintz et al. | |
| 2019/0110839 A1 | 4/2019 | Rafii-Tari et al. | |
| 2019/0151148 A1 | 5/2019 | Alvarez et al. | |
| 2019/0167366 A1 | 6/2019 | Ummalaneni | |
| 2019/0175009 A1 | 6/2019 | Mintz | |
| 2019/0175062 A1 | 6/2019 | Rafii-Tari et al. | |
| 2019/0175799 A1 | 6/2019 | Hsu | |
| 2019/0183585 A1 | 6/2019 | Rafii-Tari et al. | |
| 2019/0183587 A1 | 6/2019 | Rafii-Tari et al. | |
| 2019/0216548 A1 | 7/2019 | Ummalaneni | |
| 2019/0216576 A1 | 7/2019 | Eyre | |
| 2019/0223974 A1 | 7/2019 | Romo | |
| 2019/0228525 A1 | 7/2019 | Mintz et al. | |
| 2019/0246882 A1 | 8/2019 | Graetzel et al. | |
| 2019/0255359 A1 | 8/2019 | Benali | |
| 2019/0262086 A1 | 8/2019 | Connolly et al. | |
| 2019/0269468 A1 | 9/2019 | Hsu et al. | |
| 2019/0274764 A1 | 9/2019 | Romo | |
| 2019/0290109 A1 | 9/2019 | Agrawal et al. | |
| 2019/0298160 A1 | 10/2019 | Ummalaneni et al. | |
| 2019/0298460 A1 | 10/2019 | Al-Jadda | |
| 2019/0298465 A1 | 10/2019 | Chin | |
| 2019/0336238 A1 | 11/2019 | Yu | |
| 2019/0365201 A1 | 12/2019 | Noonan et al. | |
| 2019/0365209 A1 | 12/2019 | Ye et al. | |
| 2019/0365479 A1 | 12/2019 | Rafii-Tari | |
| 2019/0365486 A1 | 12/2019 | Srinivasan et al. | |
| 2019/0374297 A1 | 12/2019 | Wallace et al. | |
| 2019/0375383 A1 | 12/2019 | Alvarez | |
| 2019/0380787 A1 | 12/2019 | Ye | |
| 2019/0380797 A1 | 12/2019 | Yu | |
| 2020/0000533 A1 | 1/2020 | Schuh | |
| 2020/0022767 A1 | 1/2020 | Hill | |
| 2020/0039086 A1 | 2/2020 | Meyer | |
| 2020/0046434 A1 | 2/2020 | Graetzel | |
| 2020/0054408 A1 | 2/2020 | Schuh et al. | |
| 2020/0060516 A1 | 2/2020 | Baez | |
| 2020/0085516 A1 | 3/2020 | DeFonzo | |
| 2020/0093549 A1 | 3/2020 | Chin | |
| 2020/0093554 A1 | 3/2020 | Schuh | |
| 2020/0100845 A1 | 4/2020 | Julian | |
| 2020/0100853 A1 | 4/2020 | Ho | |
| 2020/0100855 A1 | 4/2020 | Leparmentier | |
| 2020/0101264 A1 | 4/2020 | Jiang | |
| 2020/0107894 A1 | 4/2020 | Wallace | |
| 2020/0121502 A1 | 4/2020 | Kintz | |
| 2020/0146769 A1 | 5/2020 | Eyre | |
| 2020/0188043 A1 | 6/2020 | Yu | |
| 2020/0206472 A1 | 7/2020 | Ma | |
| 2020/0217733 A1 | 7/2020 | Lin | |
| 2020/0222134 A1 | 7/2020 | Schuh | |
| 2020/0237458 A1 | 7/2020 | DeFonzo | |

OTHER PUBLICATIONS

NIH, National Cancer Institute, definition of "endoluminal", from the internet <https://www.cancer.gov/publications/dictionaries/cancer-terms/def/endoluminal>, accessed on Feb. 21, 2023, 1 page.

Sasaki, Kazuhito, et al. "Laparoscopic hemicolectomy for a patient with situs inversus totalis: A case report." *International journal of surgery case reports* 41 (2017): 93-96.

International Search Report and Written Opinion dated Jul. 13, 2016, for International Application No. PCT/US2016/026783, 11 pages.

* cited by examiner

513

512

511

SURGICAL SYSTEM WITH CONFIGURABLE MECHANICAL ARMS STOWABLE BENEATH A SURGICAL BED

CROSS REFERENCE TO RELATED APPLICATIONS

This application is a continuation of U.S. patent application Ser. No. 16/914,873 filed Jun. 29, 2020, now U.S. Pat. No. 12,193,769, which is a continuation U.S. patent application Ser. No. 16/195,206, filed Nov. 19, 2018, now U.S. Pat. No. 10,702,348, which is a continuation of U.S. patent application Ser. No. 15/094,179, filed Apr. 8, 2016, now U.S. Pat. No. 10,159,533, which claims priority to U.S. Provisional Application No. 62/145,418, filed Apr. 9, 2015, all of which are incorporated by reference herein as if reproduced in their entireties.

The present invention relates to medical instruments, tools, and methods that may be incorporated into a robotic system, such as those disclosed in U.S. patent application Ser. No. 14/523,760, filed Oct. 24, 2014, now U.S. Pat. No. 9,763,741, U.S. Provisional Patent Application No. 62/019,816, filed Jul. 1, 2014, U.S. Provisional Patent Application No. 62/037,520, filed Aug. 14, 2014, and U.S. Provisional Patent Application No. 62/057,936, filed Sep. 30, 2014, the entire contents of which are incorporated herein by reference.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD OF THE INVENTION

The field of the present invention relates to a robotics platform that may be used in a number of surgical procedures. More particularly, the field of the invention pertains to robotic platforms that enable robotically-controlled tools to perform diagnostic and therapeutic surgical procedures.

BACKGROUND OF THE RELATED ART

Use of robotic technologies presents a number of advantages over traditional, manual surgery procedures. In addition to other advantages, robotic surgeries often allow for greater precision, control, and access. Despite these advantages, however, the pre-existing robotics platforms have built-in limitations that are tied to their structural designs and underpinnings. In the absence of a truly flexible system, hospitals and health care practitioners are forced to acquire a variety of robotic systems in order to robotically perform a variety of procedures. The high capital costs, combined with the relatively specialization of the systems, have slowed adoption of robotics platforms for surgery.

Accordingly, there is a need for a robotics platform that is configurable for a number of procedures.

BRIEF SUMMARY OF THE INVENTION

In general, the present invention provides a medical device that comprises a rail having a rounded path, a carriage configured to translate along the rail, the carriage being operatively coupled to the rail, a robotic arm operatively coupled to the carriage, and a horizontal platform proximate to the rail, wherein the robotic arms are configured to perform medical procedures on a patient on the platform. In one aspect, the rounded path is U-shaped. In one aspect, the U-shaped path comprises of a first leg and a second leg, wherein the first leg is longer than the second leg. In another aspect, the rail is configured around a central base. In one aspect, the central base is shaped like a column.

In another aspect, a horizontal platform is operatively coupled to the top of the base. In one aspect, the rail is disposed below the platform. In one aspect, the rail is around the platform. In one aspect, the arm is configured to be angled over platform.

In another aspect, the platform is a surgical bed, configured to support the weight of a patient. In one aspect, the surgical bed comprises a first part and a second part, wherein the second part is configured to articulate relative to the first part.

In another aspect, the rail is configured around a horizontal platform. In one aspect, the platform is a surgical bed, configured to support the weight of a patient.

In another aspect, the rounded path is circular. In one aspect, the rail is disposed below the platform. In one aspect, the rail is around the platform.

BRIEF DESCRIPTION OF THE DRAWINGS

The invention will be described, by way of example, and with reference to the accompanying diagrammatic drawings, in which.

DETAILED DESCRIPTION OF THE DRAWINGS

Although certain preferred embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

In clinical applications, the design of the base of the robotics platform often constrains the types of procedures that may be performed by the system. For example, in a system where robotic appendages are only available around the abdomen, urology procedures are precluded from being performed. Likewise, robotic arms below the abdomen may not be useful for laparoscopic procedures. Accordingly, the present invention provides a flexible design such that robotic arms may be delivered to multiple access points in a patient around a surgical bed.

Figure 1:
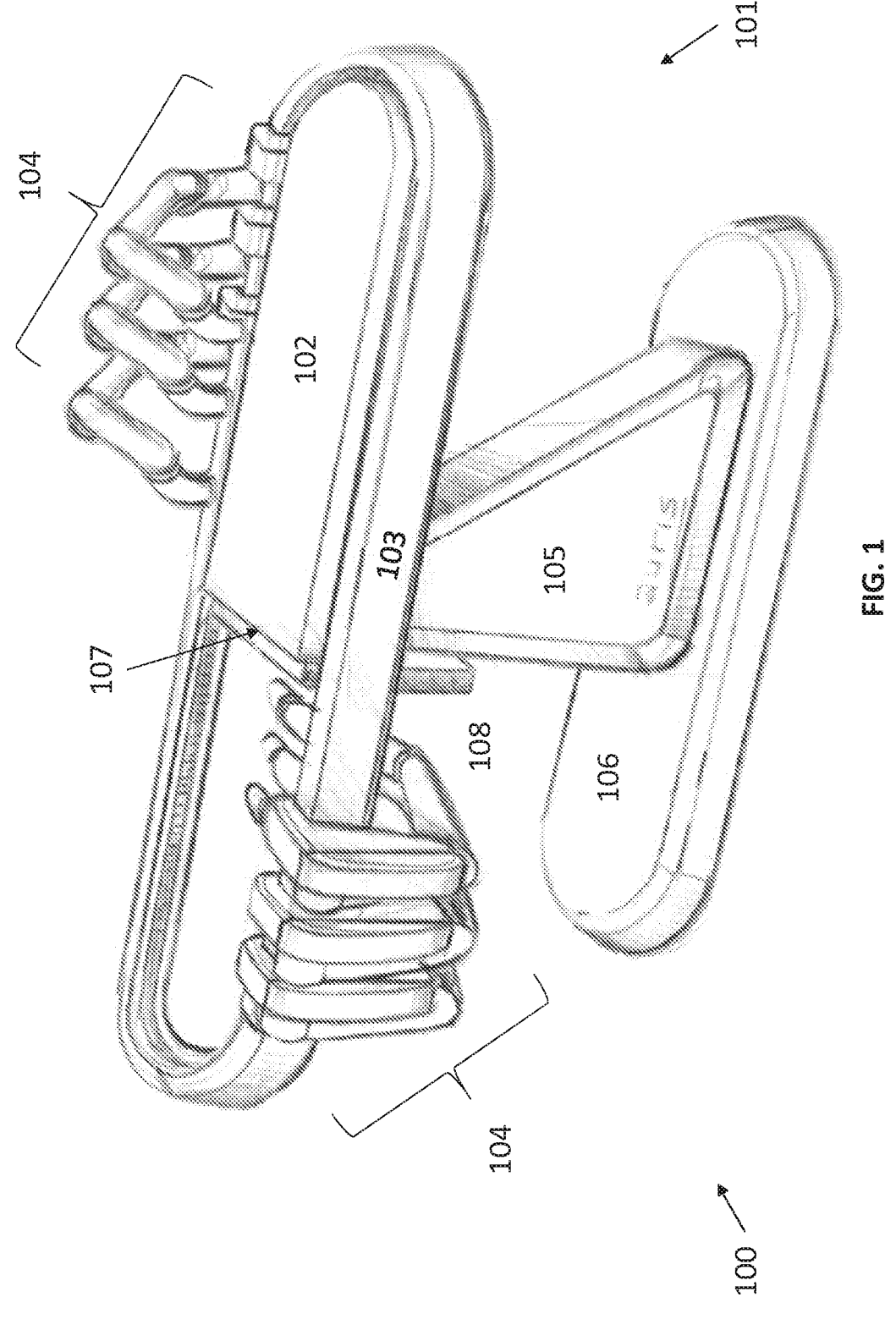
FIG. 1 illustrates a surgical bed with an oval track for robotic arms along the edge of the bed, consistent with an embodiment of the present invention.

FIG. 1 illustrates a surgical bed with an oval track for robotic arms along the edge of the bed, consistent with an embodiment of the present invention. As shown in the isometric view 100 of the robotic system 101, the system 101 comprises of a surgical bed 102, a rail 103 for mechanical arms 104, a support stand 105, and a system base 106. The surgical bed allows for a hinge 107 such that a portion 108 of surgical bed 102 may be declined at a different angle from the rest of the bed. This may be desirable for certain operations, such as when performing a procedure that requires access a patient's lower abdomen, such as ureteroscopy or hysteroscopy.

Encircling the surgical bed 102, the rail 103 provides a structure to slidingly translate the mechanical arms 104 to a desired location around the surgical bed 102. The rail 103, which may be referred to as a "track", and the mechanical arms 104 may be slidingly translated along it in order to facilitate access for the arms. The rail 103 also provides allows for the conveyance and reception of power, controls, fluidics, aspiration to the mechanical arms 104. The rail 103 may be fully circular and surround all sides of the surgical bed 102.

The mechanical arms 104 may be operatively coupled to the rail 103. The mechanical arms may also be robotic. The translation of the mechanical arms 104 may be actuated either manually or robotically. The mechanical arms 104 may be coupled independently to the rail 103 or in groups via a mechanical carriage that may slide around the rail 103. In addition to providing structural support to the mechanical arms 104, the carriage may be used to convey and receive power, controls, fluidics, and aspiration to and from the arms 104 to the rail 103.

In combination or individually, the support stand 105 and the system base 106 may be used to house electronics, fluidics, pneumatics, and aspiration. The electronics may be used from control, localization, navigation of the arms 104. Thus, as a robotically-driven platform, system 101 provides for a comprehensive surgical bed and tool solution that may be used to perform any number of procedures around a patient.

Figure 2:
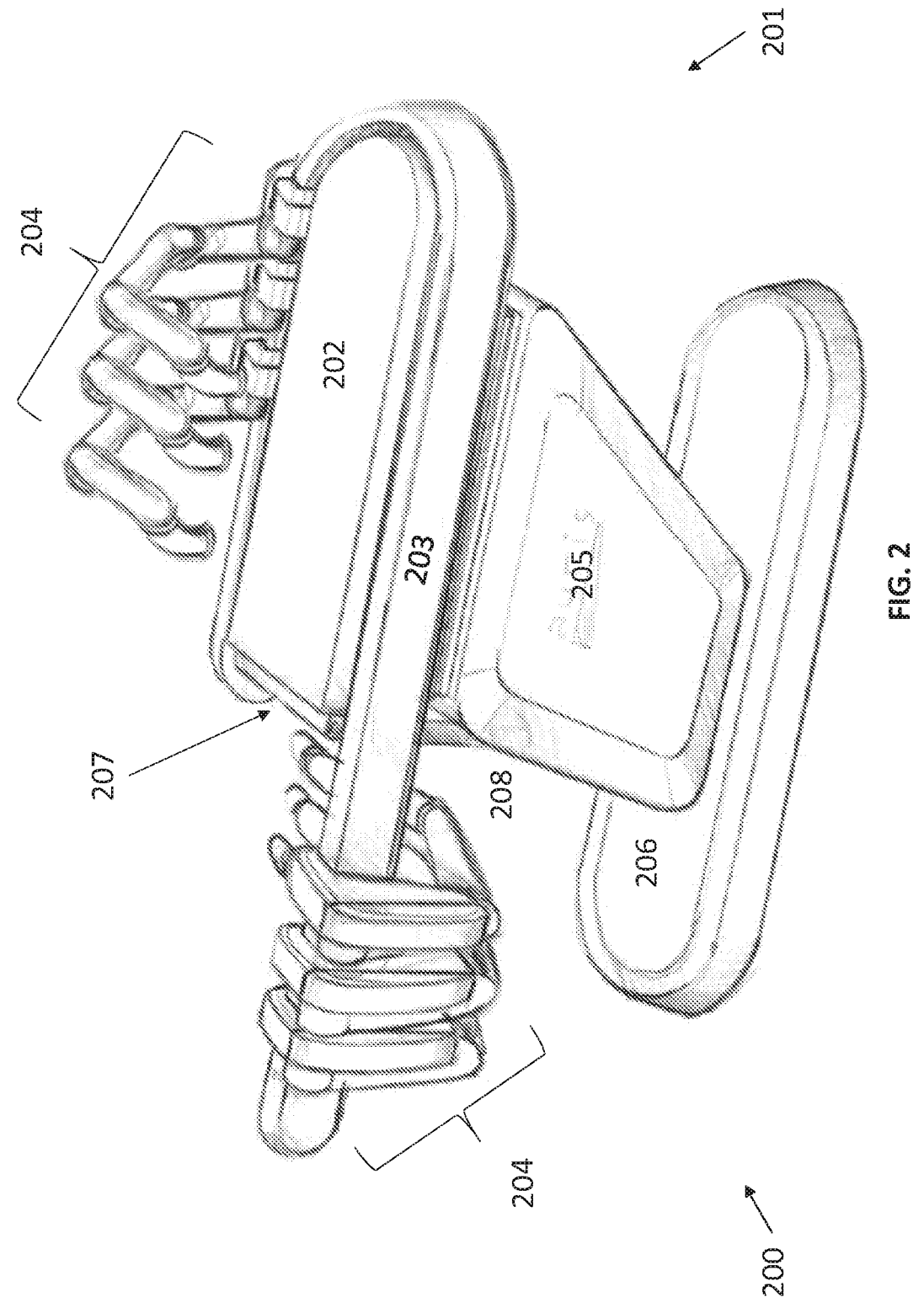
FIG. 2 illustrates a surgical bed with a U-shaped track for robotic arms along the edge of the bed, consistent with an embodiment of the present invention.

FIG. 2 illustrates a surgical bed with a U-shaped track for robotic arms along the edge of the bed, consistent with an embodiment of the present invention. As shown in the isometric view 200 of the robotic system 201, the system 201 comprises of a surgical bed 202, a rail 203 for mechanical arms 204, a support stand 205, and a system base 206. Like in system 101, the surgical bed 202 allows for a hinge 207 such that a portion 208 of surgical bed 202 may be declined at a different angle from the rest of the bed 202. As discussed earlier, this may be desirable for certain operations, such as when performing a procedure that requires access a patient's lower abdomen, such as ureteroscopy, hysteroscopy, or colonoscopy.

Running along the surgical bed 202, the rail 203 provides a structure to slidingly translate the mechanical arms 204 to a desired location around the surgical bed 202. Unlike rail 103, rail 203 uses a U-shape that enhances access the surgical bed 202. This may provide advantages when position the patient and accessing operative sites on a patient's lower abdomen. The longer leg of the rail 203 allows for the mechanical arms to be aligned to convey a medical instrument into the patient by means of a "virtual rail" such as one discussed in the aforementioned patent applications. As before, the rail 203 may be referred to as a "track", and the mechanical arms 204 may be slidingly translated along it in order to facilitate access for the arms. The rail 203 also provides allows for the conveyance and reception of power, controls, fluidics, aspiration to the mechanical arms 204.

In combination or individually, the support stand 205 and the system base 206 may be used to house electronics, fluidics, pneumatics, and aspiration. The electronics may be used from control, localization, navigation of the arms 204. Thus, as a robotically-driven platform, system 201 provides for an improved, comprehensive surgical bed and tool solution that may be used to perform any number of procedures around a patient.

As deployed, the mechanical arms 104 from system 101 and mechanical arms 204 and system 201 are positioned to perform endolumenal procedures to access the access points in the lower abdomen (e.g., urology, ureteroscopy, hysteroscopy, or colonoscopy) and upper abdomen (e.g., bronchoscopy, gastro-intestinal).

Figure 3:
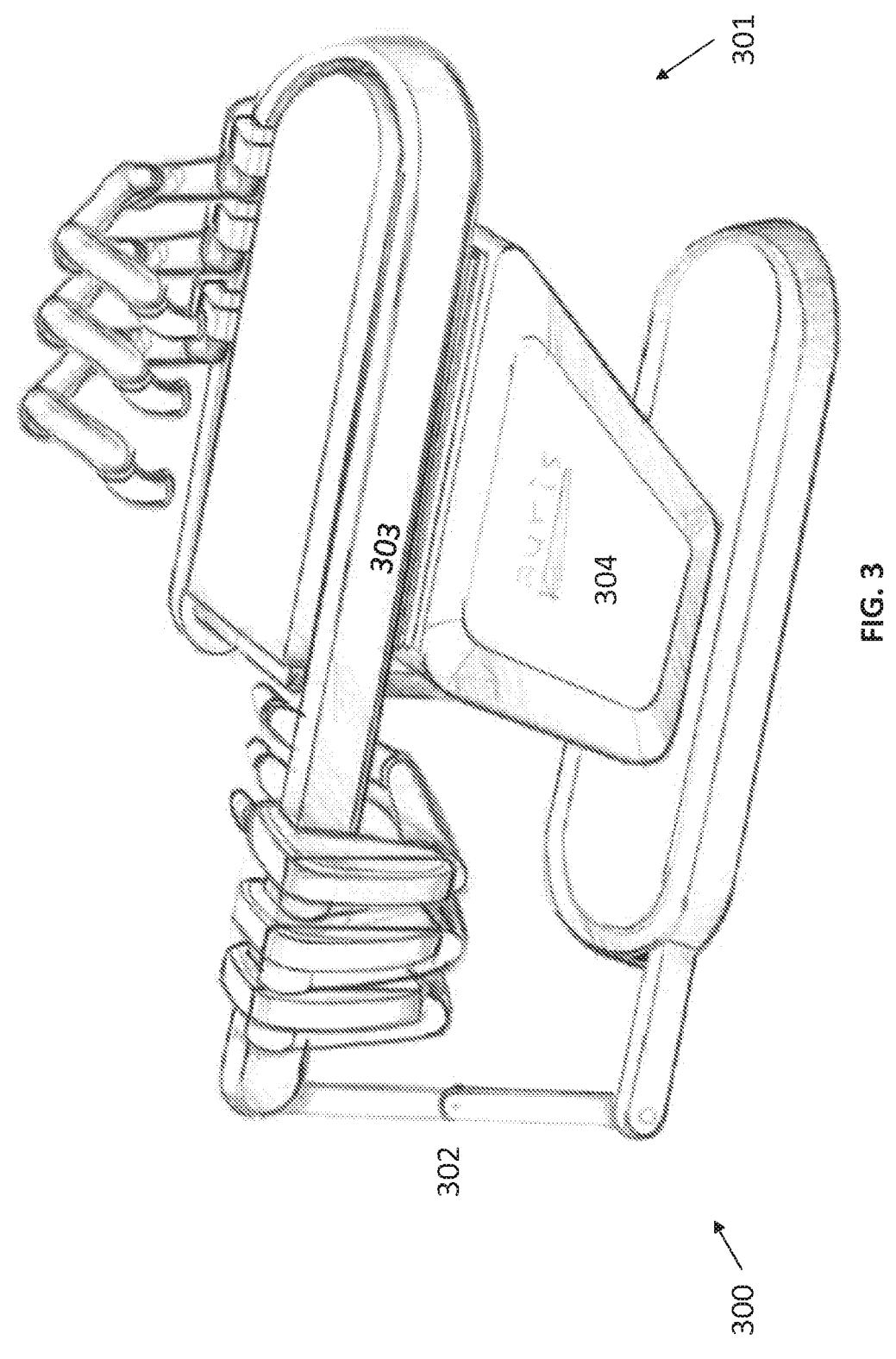
FIG. 3 illustrates an alternative robotics platform to system 201 from FIG. 2.

FIG. 3 illustrates an alternative robotics platform to system 201 from FIG. 2. As shown in isometric view 300, system 301 incorporates all the technologies disclosed with respect to system 201 with the additional vertical translation apparatus 302 that enables control over the vertical height of the rail 303. System 301 thus allows for vertical translation of the rail 303 relative to the support stand 304.

Figure 4:
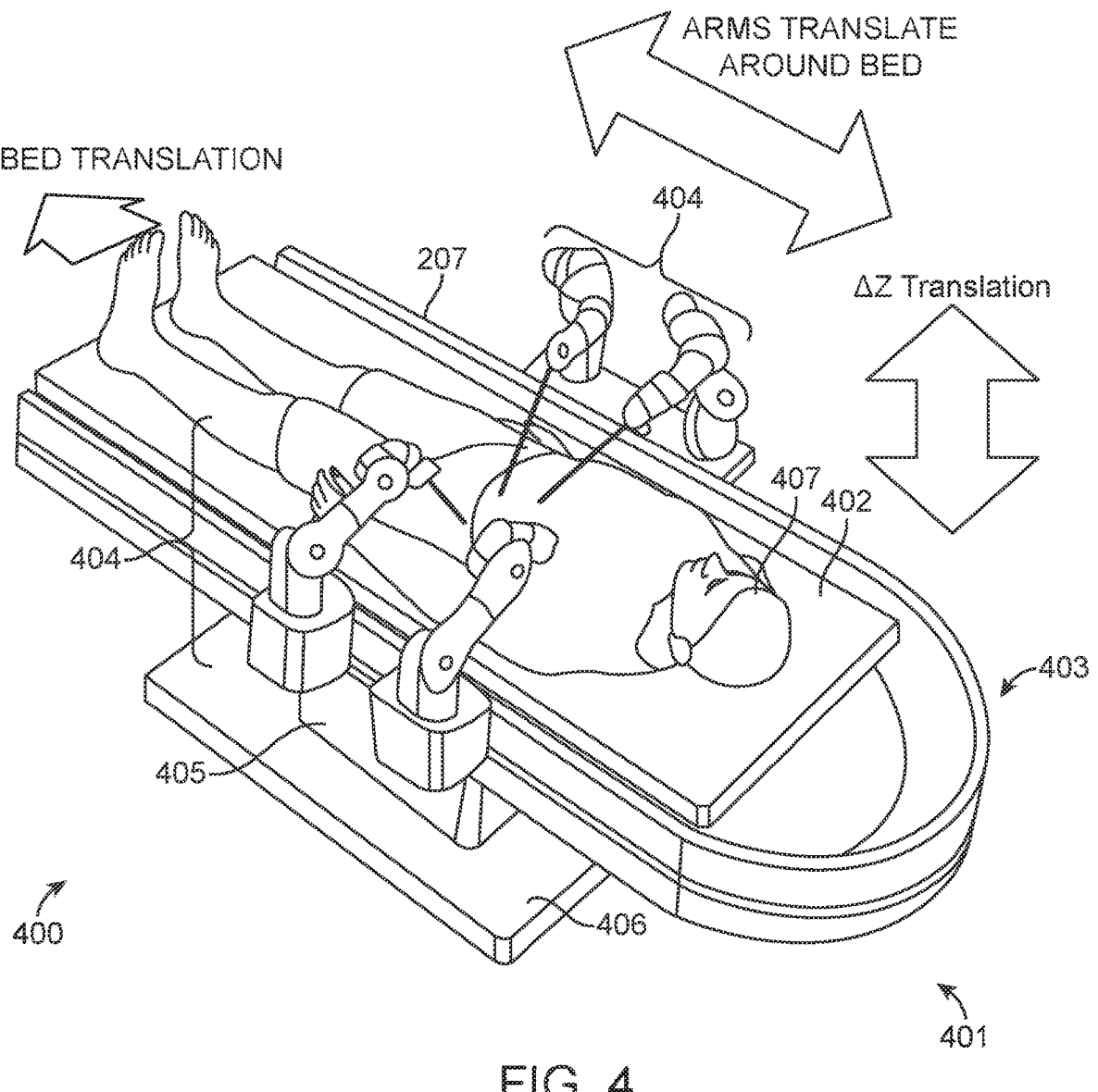
FIG. 4 illustrates a surgical bed with a rounded track for robotic arms along the edge of the bed, consistent with an embodiment of the present invention.

FIG. 4 illustrates a surgical bed with a rounded track for robotic arms along the edge of the bed, consistent with an embodiment of the present invention. As shown in the isometric view 400 of the robotic system 401, the system 401 comprises of a surgical bed 402, a rail 403 (or "track")

for mechanical arms 404, a support stand 405, and a system base 406. The surgical bed 402 may be configured to translate horizontally to position patient 407 relative to mechanical arms 404.

Encircling the surgical bed 402, the rail 403 provides a structure to slidingly translate the mechanical arms 404 to a desired location around the surgical bed 402. The rail 403, which may be referred to as a "track", and the mechanical arms 404 may be slidingly translated along it in order to facilitate access for the arms. The rail 403 also provides allows for the conveyance and reception of power, controls, fluidics, aspiration to the mechanical arms 404.

The mechanical arms 404 may be operatively coupled to the rail 403. The mechanical arms 404 may also be robotic. The translation of the mechanical arms 404 may be actuated cither manually or robotically. The mechanical arms 404 may be coupled independently to the rail 403 or in groups via a mechanical carriage that may slide around the rail 403. In addition to providing structural support to the mechanical arms 404, the carriage may be used to convey and receive power, controls, fluidics, and aspiration to and from the arms 404 to the rail 403. The ability to translate the arms 404 and translate the bed 402 allows for nearly unlimited access to different portions of the anatomy of patient 407.

In combination or individually, the support stand 405 and the system base 406 may be used to house electronics, fluidics, pneumatics, and aspiration. The electronics may be used from control, localization, navigation of the arms 404. Thus, as a robotically-driven platform, system 401 provides for a comprehensive surgical bed and tool solution that may be used to perform any number of procedures around a patient. The support stand 405 may also translate vertically, allowing for easier access to the patient 407 and operative site.

As deployed in view 400, mechanical arms 404 may be positioned to access the abdomen of patient 407 for laparoscopic procedures.

Figure 5A:
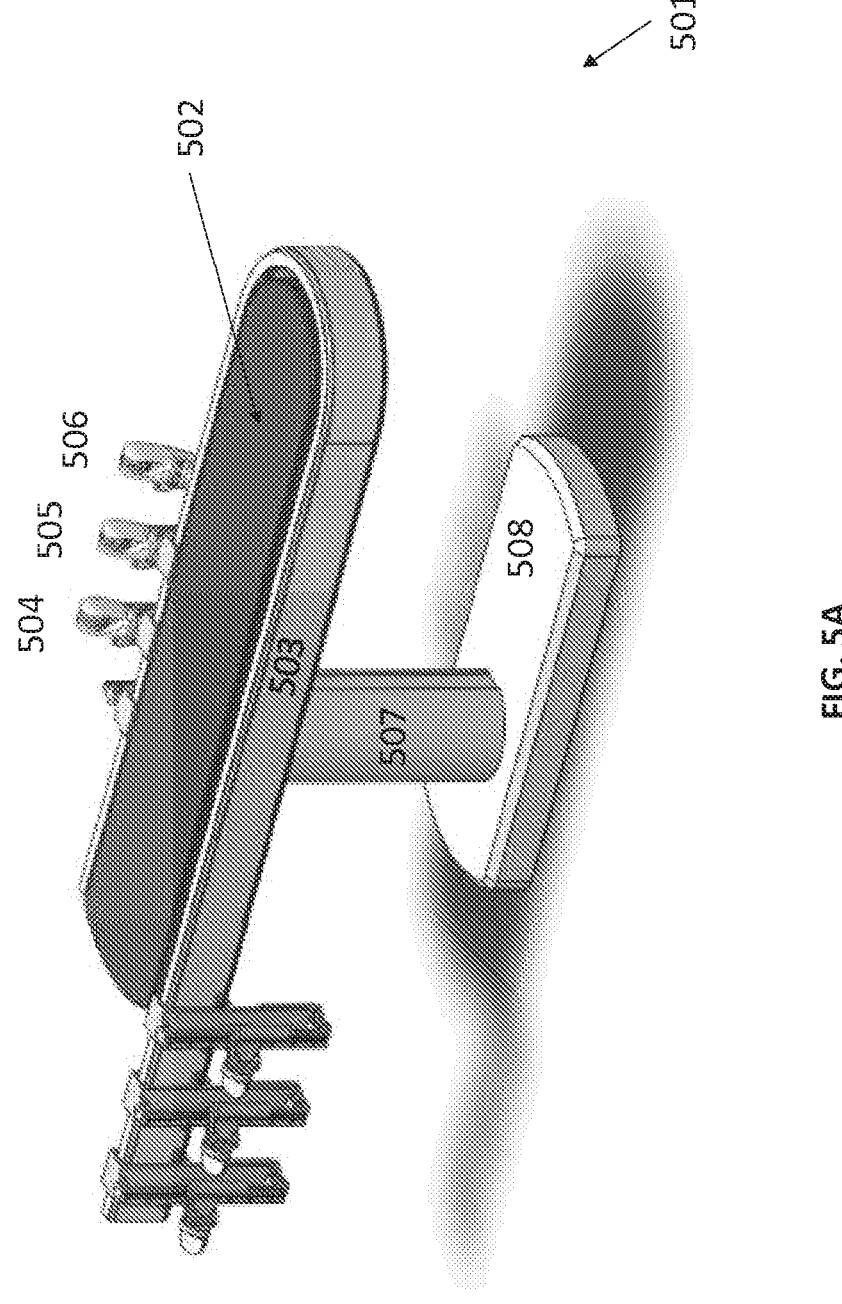
FIG. 5A illustrates a surgical bed with a rounded track for robotic arms along the edge of the bed, consistent with an embodiment of the present invention.

FIG. 5A illustrates a surgical bed with a rounded track for robotic arms along the edge of the bed, consistent with an embodiment of the present invention. As shown in the isometric view 500 of the robotic system 501, the system 501 comprises of a surgical bed 502, a rail 503 (or "track") for mechanical arms 504, 505, 506, a support stand 507, and a system base 508. The surgical bed 502 may be configured to translate horizontally to position a patient relative to mechanical arms 504, 505, 506.

Encircling the surgical bed 502, the rail 503 provides a structure to slidingly translate the mechanical arms 504, 505, 506 to a desired location around the surgical bed 502. The rail 503, which may be referred to as a "track", and the mechanical arms 504, 505, 506 may be slidingly translated along it in order to facilitate access for the arms 504, 505, 506. The rail 503 also provides allows for the conveyance and reception of power, controls, fluidics, aspiration to the mechanical arms 504, 505, 506.

The mechanical arms 504, 505, 506 may be operatively coupled to the rail 503. The mechanical arms 504, 505, 506 may also be robotic. The translation of the mechanical arms 504, 505, 506 may be actuated either manually or robotically. The mechanical arms 504, 505, 506 may be coupled independently to the rail 503 or individually or in groups via mechanical carriages that may slide around the rail 503. In addition to providing structural support to the mechanical arms 504, 505, 506 a carriage may be used to convey and receive power, controls, fluidics, and aspiration to and from the arms 504, 505, 506 to the rail 503. The ability to translate the arms 504, 505, 506 and translate the bed 502 allows for nearly unlimited access to different portions of the anatomy of a patient.

In combination or individually, the support stand 507 and the system base 508 may be used to house electronics, fluidics, pneumatics, and aspiration. The electronics may be used from control, localization, navigation of the arms 504, 505, 506. Thus, as a robotically-driven platform, system 501 provides for a comprehensive surgical bed and tool solution that may be used to perform any number of procedures around a patient. The support stand 507 may also translate vertically, allowing for easier access to the patient and operative site.

As deployed in view 500, mechanical arms 504, 505, 506 may be positioned to access the abdomen of patient for laparoscopic procedures, while the carriages on the other side of rail 503 may be positioned to hold mechanical arms to create a virtual rail for access points in the lower abdomen (e.g., urology, ureteroscopy, or hysteroscopy).

Figure 5B:
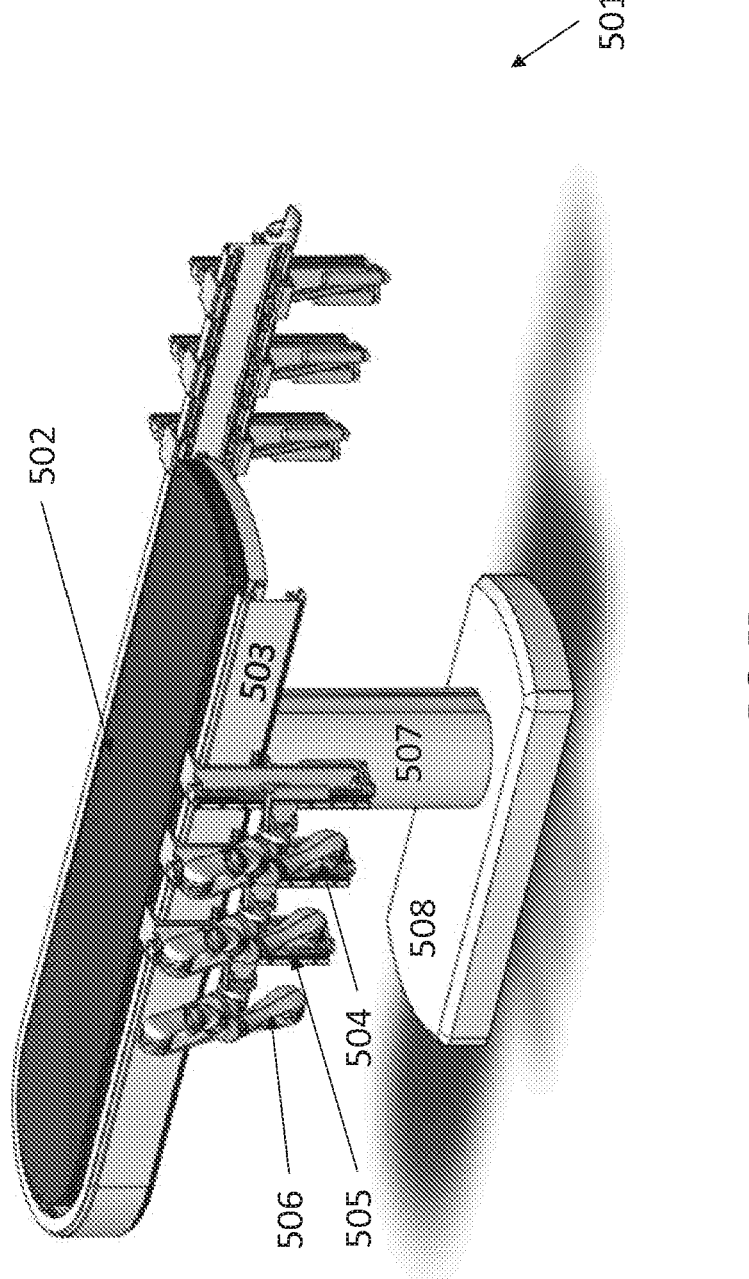
FIG. 5B illustrates the surgical bed with a rounded track from FIG. 5A, consistent with an embodiment of the present invention.

FIG. 5B illustrates the surgical bed with a rounded track from FIG. 5A, consistent with an embodiment of the present invention. Reverse isometric view 509 provides a different perspective of the robotic system 501, surgical bed 502, rail 503 (or "track") for mechanical arms 504, 505, 506 a support stand 507, and a system base 508.

Figure 5C:
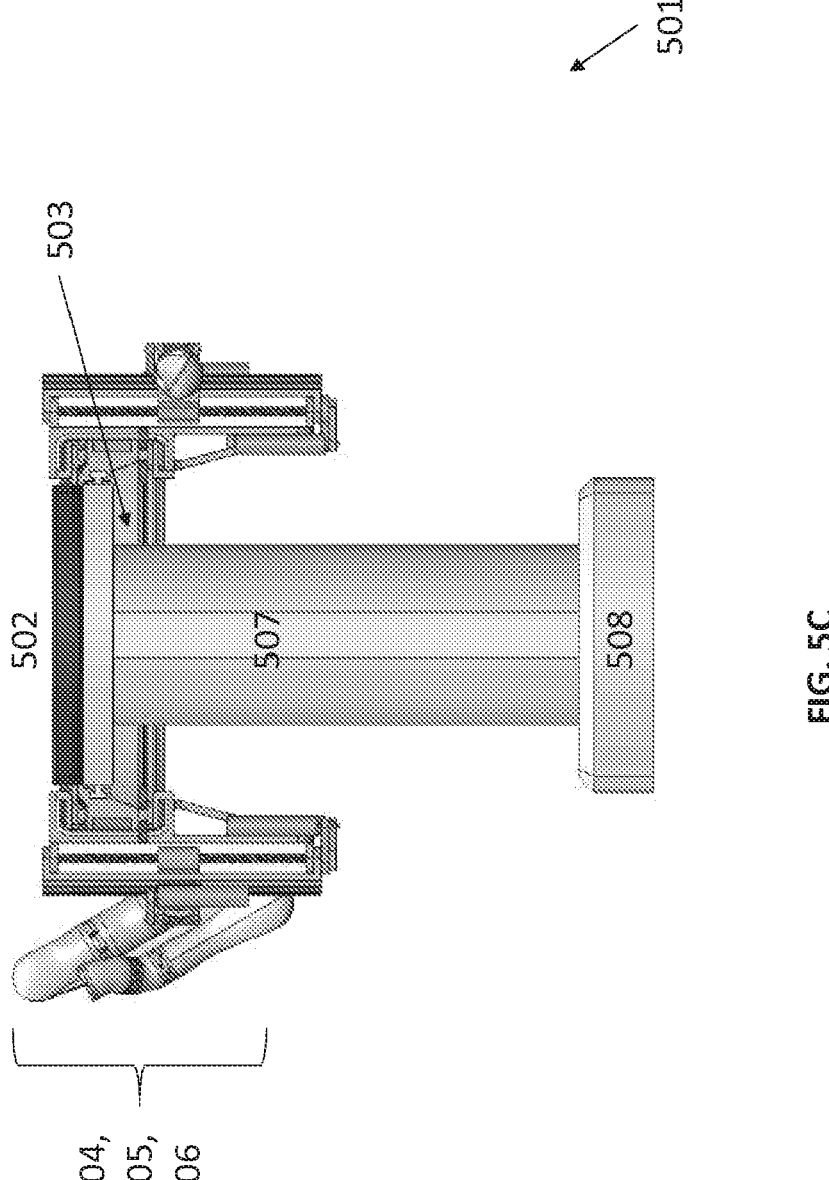
FIG. 5C illustrates the surgical bed with a rounded track from FIGS. 5A, 5B, consistent with an embodiment of the present invention.

FIG. 5C illustrates the surgical bed with a rounded track from FIGS. 5A, 5B, consistent with an embodiment of the present invention. Rear view 510 provides a different perspective of the robotic system 501, surgical bed 502, rail 503 (or "track") for mechanical arms 504, 505, 506, support stand 507, and a system base 508.

Figure 5D:
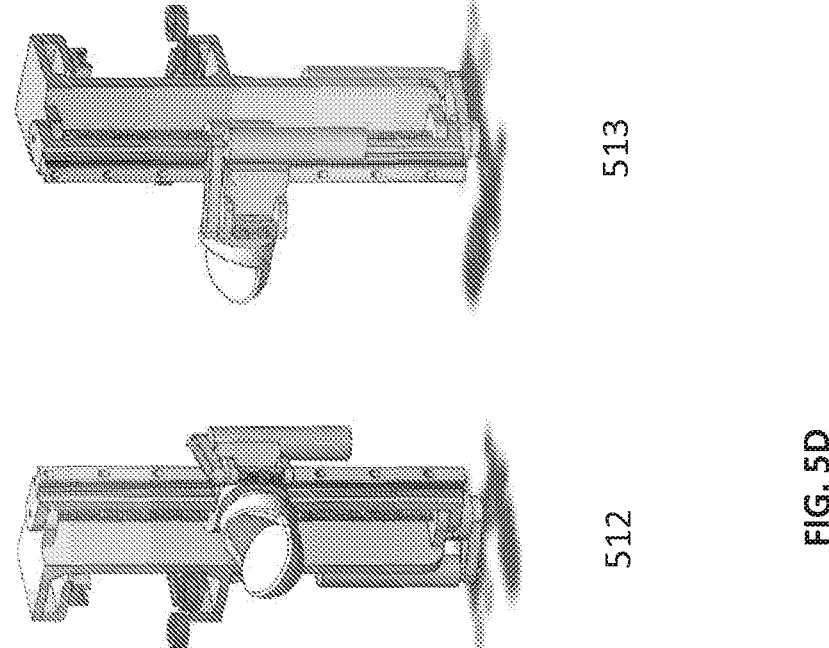
FIG. 5D illustrates several views of carriages for mechanical arms used in system 501 from FIGS. 5A, 5B.
Figure 5D:
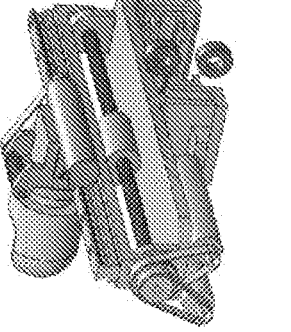

FIG. 5D illustrates several views of carriages for mechanical arms used in system 501 from FIGS. 5A, 5B, 5C, consistent with an embodiment of the present invention. Side views 511, 512, 513 provide different perspectives on a mechanically-driven carriage in system 501.

Figure 5E:
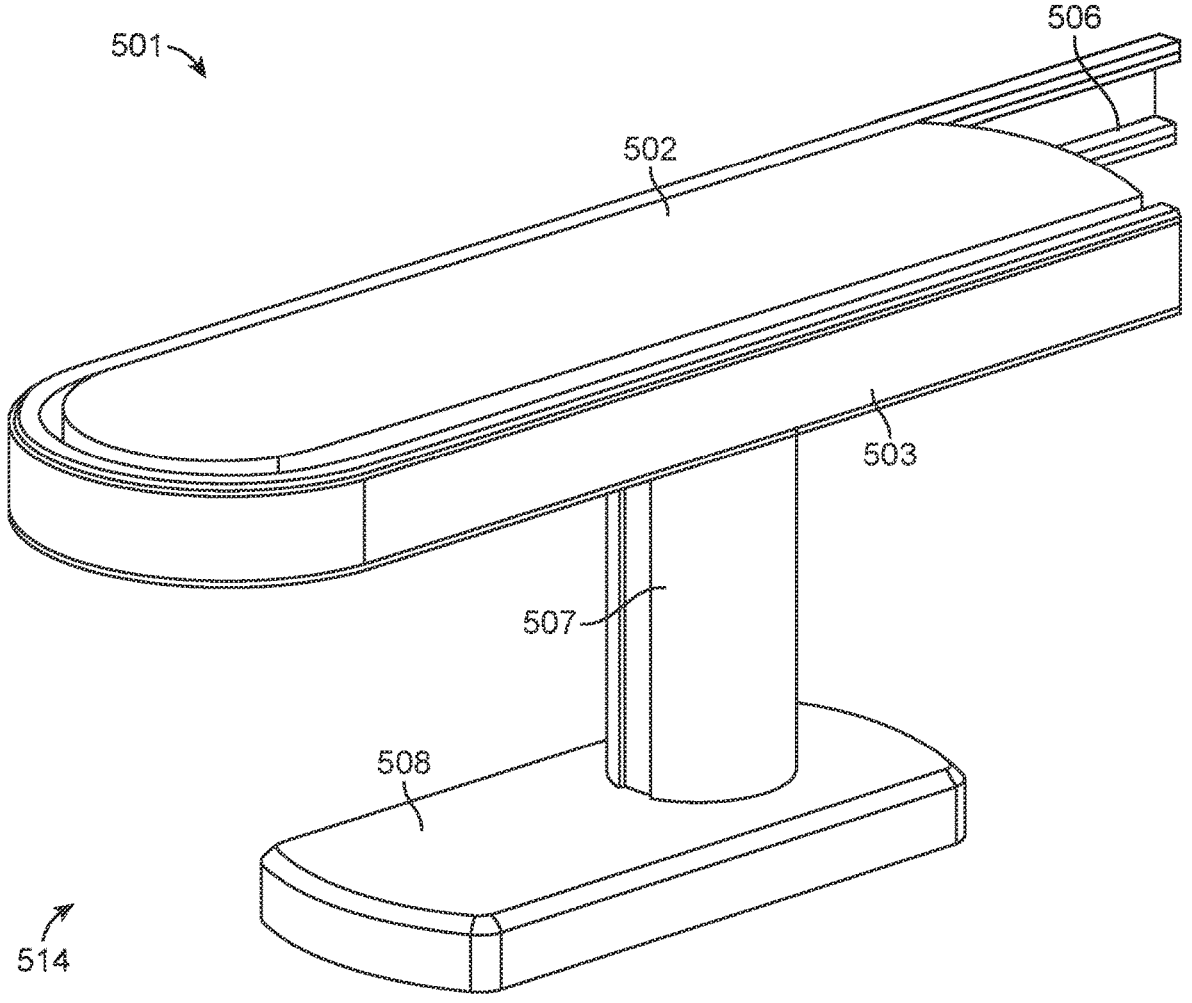
FIG. 5E illustrates the surgical bed with a rounded track from FIG. 5A, consistent with an embodiment of the present invention.

FIG. 5E illustrates the surgical bed with a rounded track from FIG. 5A, consistent with an embodiment of the present invention. View 514 provides a different perspective of the robotic system 501, surgical bed 502, rail 503 (or "track"), support stand 507, and system base 508, absent mechanical arms 504, 505, 506.

Figure 6A:
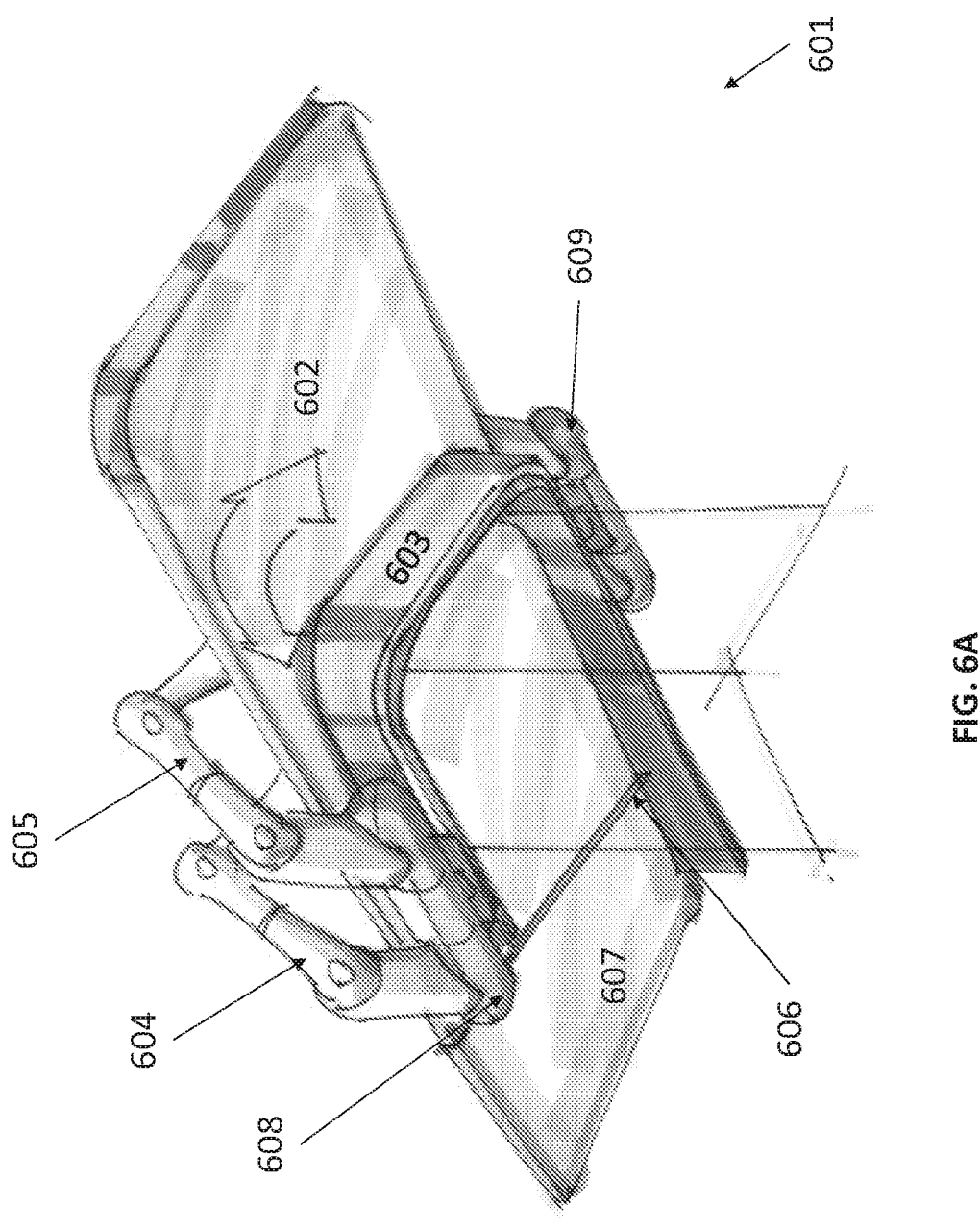
FIGS. 6A and 6B illustrate a surgical bed with a rounded track for robotic arms along the edge of the bed, consistent with an embodiment of the present invention.

FIG. 6A illustrates a surgical bed with a rounded track for robotic arms along the edge of the bed, consistent with an embodiment of the present invention. As shown in the view 600, the system 601 comprises of a surgical bed 602, a rail 603 (or "track") for mechanical arms 604, 605. The surgical bed 602 may be configured to translate horizontally to position a patient relative to mechanical arms 604, 605. The surgical bed 602 allows for a hinge 606 such that a portion 607 of surgical bed 602 may be declined at a different angle from the rest of the bed 602. As discussed earlier, this may be desirable for certain operations, such as when performing a procedure that requires access a patient's lower abdomen, such as ureteroscopy, hysteroscopy, or colonoscopy.

Underneath the surgical bed 602, the rail 603 provides a structure to slidingly translate the mechanical arms 604, 605 to a desired location around the surgical bed 602. The rail 603, which may be referred to as a "track", and the mechanical arms 604, 605 may be slidingly translated along it in order to facilitate access for the arms 604, 605. The rail 603 also provides allows for the conveyance and reception of power, controls, fluidics, aspiration to the mechanical arms 604, 605. As shown in FIG. 6A, there may be a shorter leg and longer leg portion of the U-shape rail 603. In some embodiments, the rail 603 may be fully circular, rather than a U-shaped.

The mechanical arms 604, 605 may be operatively coupled to the rail 603. The mechanical arms 604, 605 may also be robotic. The translation of the mechanical arms 604, 605 may be actuated either manually or robotically. The mechanical arms 604, 605 may be coupled independently to the rail 603 or individually or in groups (as shown) via a mechanical carriage 608 that may slide around the rail 603. In addition to providing structural support to the mechanical arms 604, 605, the carriage 606 may be used to convey and receive power, controls, fluidics, and aspiration to and from the arms 604, 605 to the rail 603. The ability to translate the arms 604, 605 and translate the bed 602 allows for nearly unlimited access to different portions of the anatomy of a patient.

Not shown, system 601 may also incorporate a support stand and the system base to house electronics, fluidics, pneumatics, and aspiration. The electronics may be used from control, localization, navigation of the arms 604, 605. Thus, as a robotically-driven platform, system 601 provides for a comprehensive surgical bed and tool solution that may be used to perform any number of procedures around a patient. The support stand may also translate vertically, allowing for easier access to the patient and operative site. The support stand may also support vertical translation of the rail 603 in order to facilitate access to particular anatomical access points.

As deployed in view 600, mechanical arms 604, 605 on carriage 608 may be positioned to access the abdomen of patient for procedures, such as laparoscopy or endoscopy, while a carriage 609 on the other side of rail 603 may be positioned to hold additional mechanical arms.

Figure 6B:
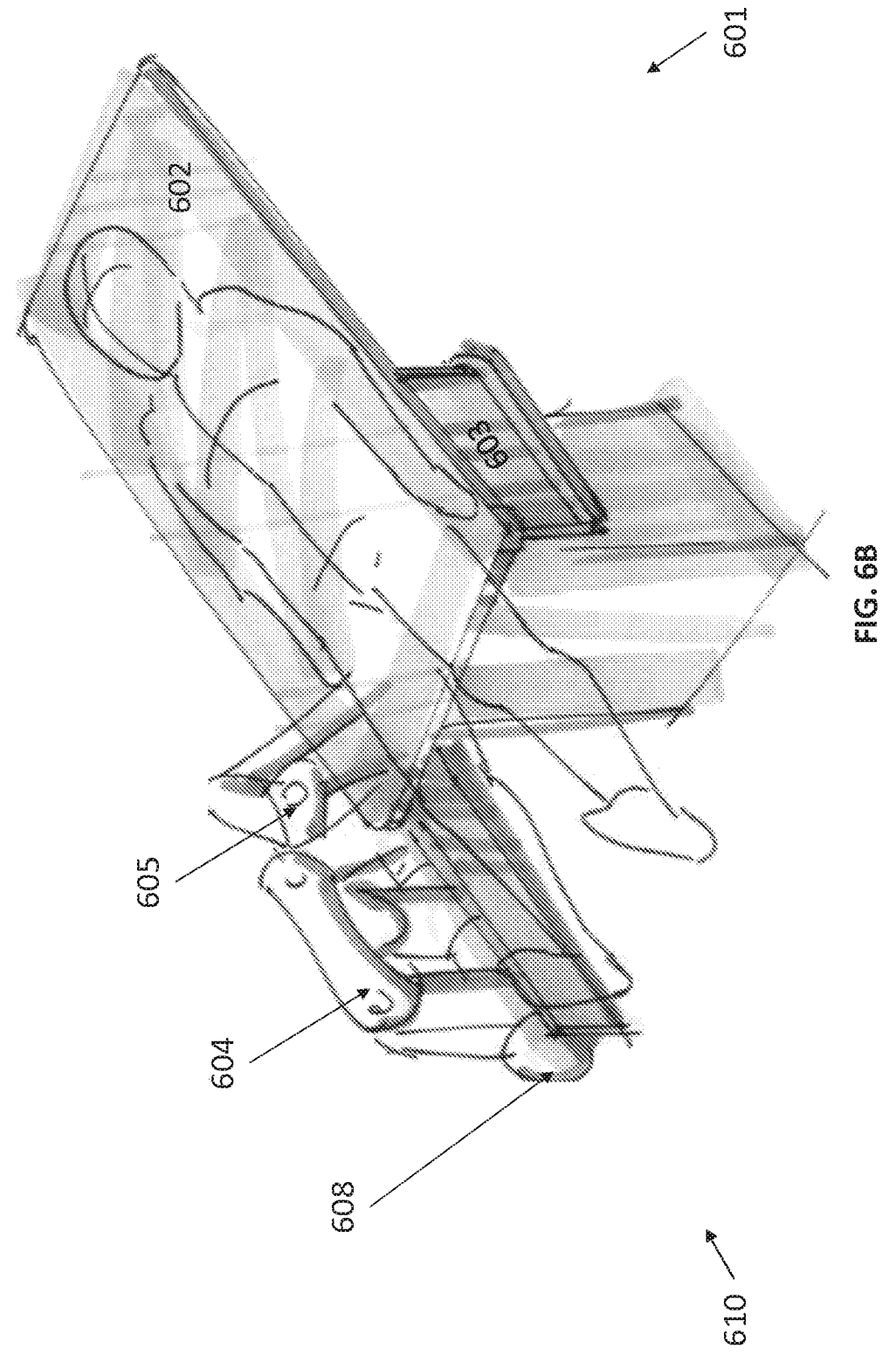

FIG. 6B illustrates the surgical bed with a rounded track from FIG. 6A. As shown in the view 610, mechanical arms 604, 605 on carriage 608 may be slidingly translated to the long side of the rail 603. View 610 also provides a view of a support base. As deployed in view 610, mechanical arms 604, 605 on carriage 608 may be positioned to form a virtual rail for access to the anatomical lumens in the lower abdomen for various procedures, such as ureteroscopy, hysteroscopy, or colonoscopy. To facilitate access surgical bed 602 has been slidingly translated forwards from the rail 603.

Figure 7A:
FIG. 7A illustrates a surgical bed with a rounded track for robotic arms underneath the edge of the bed, consistent with an embodiment of the present invention.
Figure 7A:
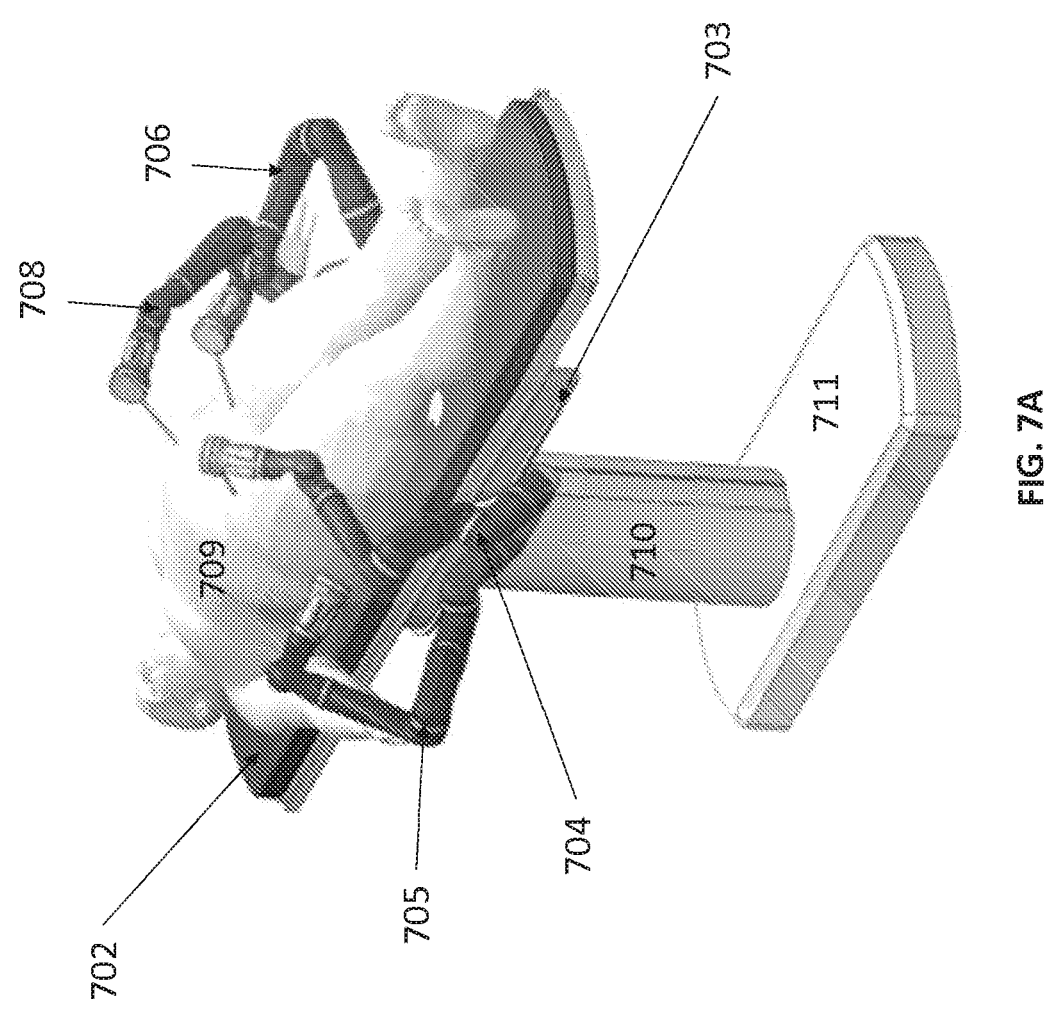

FIG. 7A illustrates a surgical bed with a rounded track for robotic arms underneath the edge of the bed, consistent with an embodiment of the present invention. As shown in the view 700, the system 701 comprises of a surgical bed 702, a rail 703 (or "track") for mechanical arms 704, 705, 706, 708. The surgical bed 702 may be configured to translate horizontally to position patient 709 relative to mechanical arms 704, 705, 706, 708. The surgical bed 702 may include a hinge such that the lower portion of surgical bed 702 may be declined at a different angle from the rest of the bed 702. As discussed earlier, this may be desirable for certain operations, such as when performing a procedure that requires access a patient's lower abdomen, such as ureteroscopy, hysteroscopy, or colonoscopy.

Underneath the surgical bed 702, the rail 703 provides a structure to slidingly translate the mechanical arms 704, 705, 706, 708 to a desired location around the surgical bed 702. The rail 703, which may be referred to as a "track" and the mechanical arms 704, 705 may be slidingly translated along it in order to facilitate access for the arms 704, 705, 706, 708. The rail 703 also provides allows for the conveyance and reception of power, controls, fluidics, aspiration to the mechanical arms 704, 705, 706, 708.

The mechanical arms 704, 705, 706, 708 may be operatively coupled to the rail 703. The mechanical arms 704, 705, 706, 708 may also be robotic. The translation of the mechanical arms 704, 705, 706, 708 may be actuated either manually or robotically. The mechanical arms 704, 705, 706, 708 may be coupled independently to the rail 703 or individually or in groups via a mechanical carriage that may slide around the rail 703. In addition to providing structural support to the mechanical arms 704, 705, 706, 708, the carriage may be used to convey and receive power, controls, fluidics, and aspiration to and from the arms 704, 705, 706, 708 to the rail 703. The ability to translate the arms 704, 705, 706, 708 and translate the bed 702 allows for nearly unlimited access to different portions of the anatomy of a patient.

System 701 may also incorporate support stand 710 and system base 711 to house electronics, fluidics, pneumatics, and aspiration. The electronics may be used from control, localization, navigation of the arms 704, 705, 706, 708. Thus, as a robotically-driven platform, system 701 provides for a comprehensive surgical bed and tool solution that may be used to perform any number of procedures around a patient. The rail 703 on support stand 710 may also translate vertically, allowing for easier access to the patient and operative site. The support stand may also telescope.

As deployed in view 700, mechanical arms 704, 705, 706, 708 may be positioned to access the abdomen of patient 709 for laparoscopic procedures, using a variety of rigid or semi-rigid laparoscopic instruments.

Figure 7B:
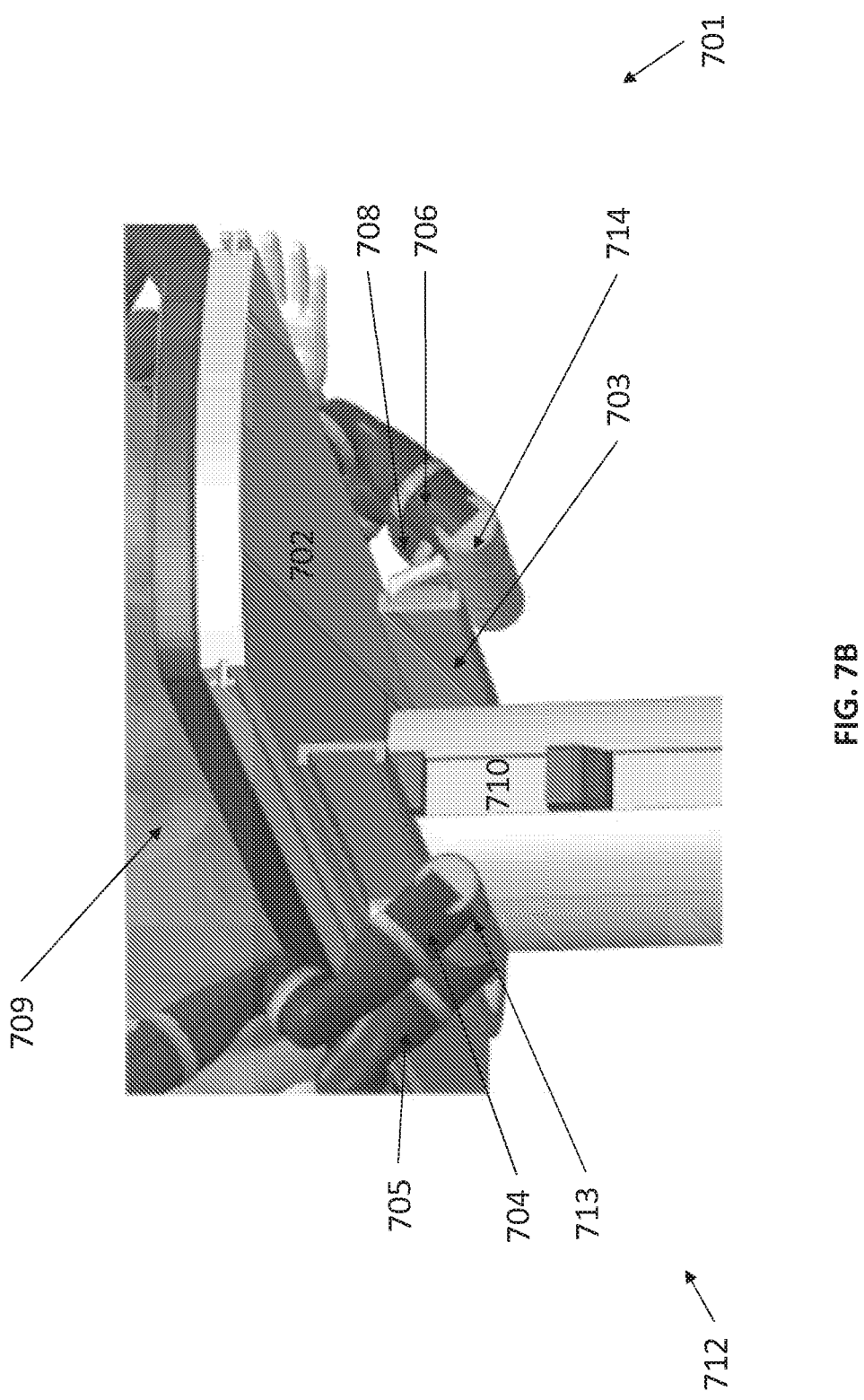
FIG. 7B illustrates the underside of the surgical bed with a rounded track from FIG. 7A.

FIG. 7B illustrates the underside of the surgical bed with a rounded track from FIG. 7A. As shown in the view 712, mechanical arms 704, 705, 706, 708 may be coupled to the rail 703 using carriages 713 and 714, which may be slidingly translated along rail 703. Carriages 713 and 714 may be oriented at various angles from rail 703 to provide an additional access to the patient 709. View 712 also provides a view of a support base 709 which shows structures to vertically translate rail 703 and bed 702.

Figure 7C:
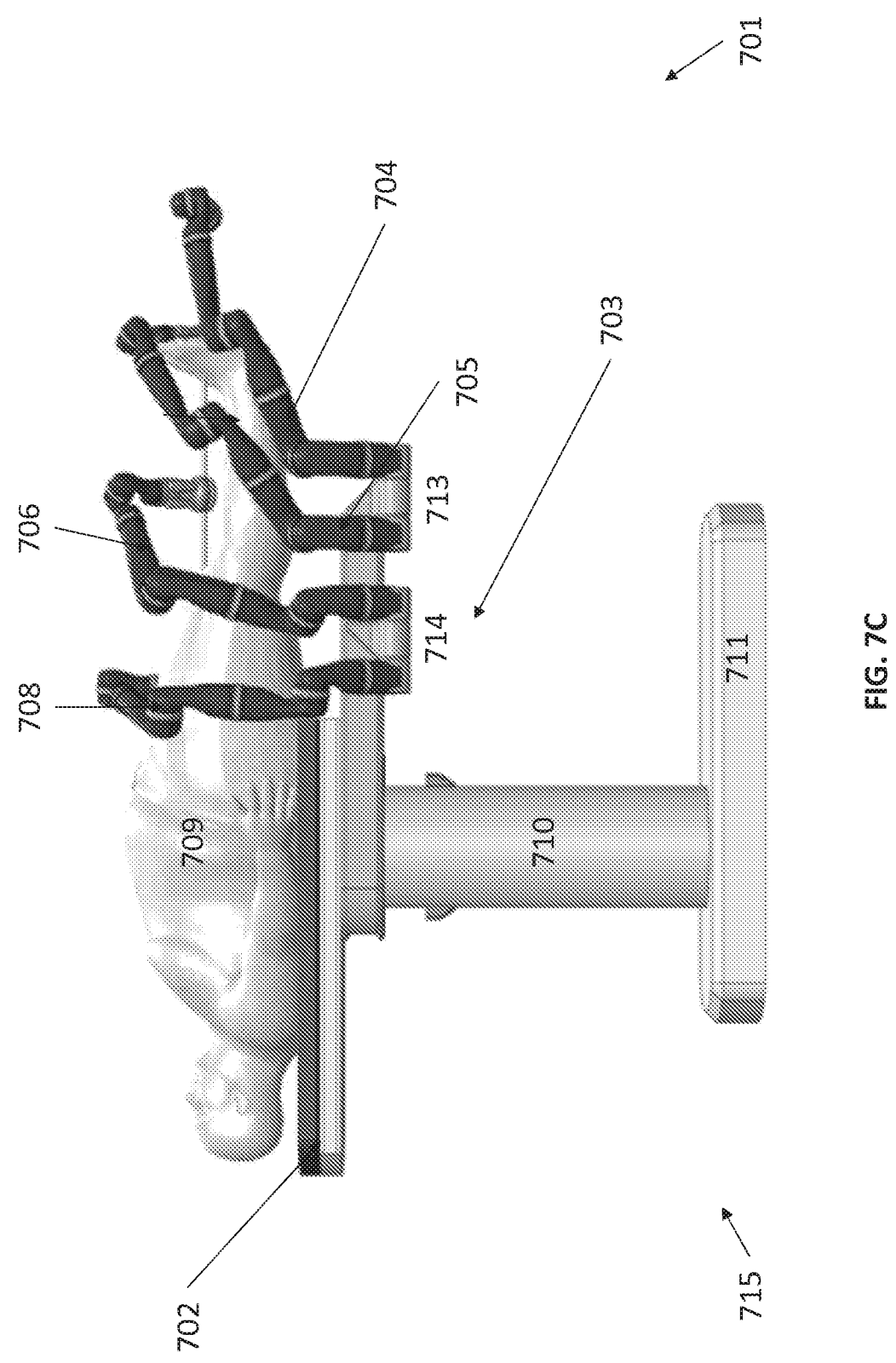
FIG. 7C illustrates the surgical bed with a rounded track from FIGS. 7A, 7B.

FIG. 7C illustrates the surgical bed with a rounded track from FIGS. 7A, 7B. As shown in side view 715, carriages 713 and 714 may be positioned along rail 703 such that mechanical arms 704, 705, 706, 708 may be arranged to form a virtual rail to guide an endoscopic device 716 into an anatomical lumen in the lower abdomen of patient 709 for a procedure such as ureteroscopy, hysteroscopy, or colonoscopy.

Figure 7D:
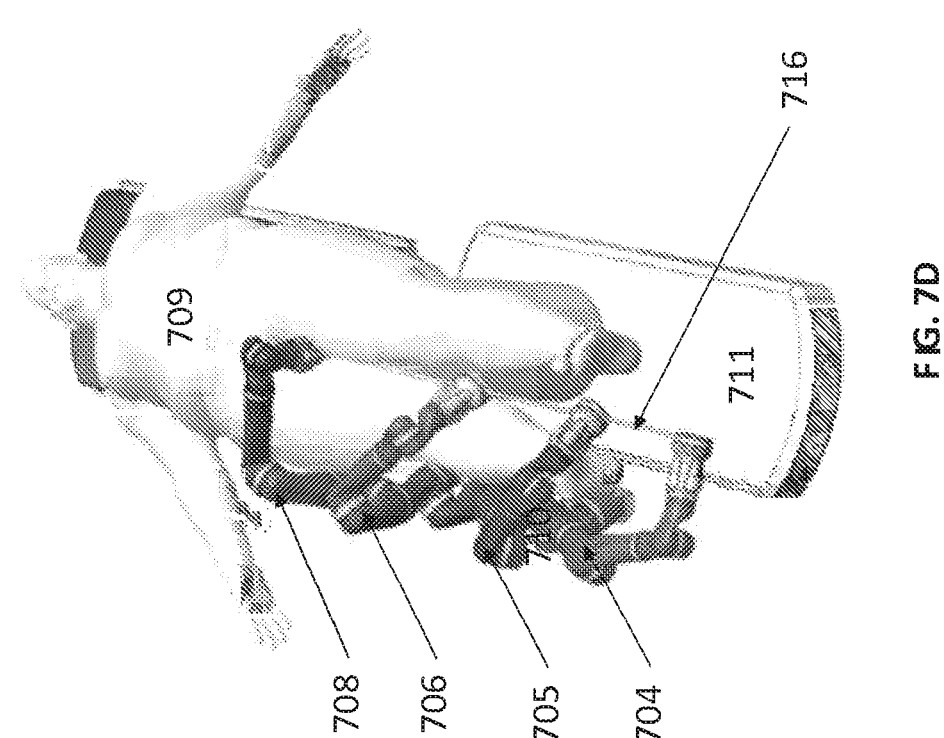
FIG. 7D illustrates the surgical bed with a rounded track from FIGS. 7A, 7B, 7C.

FIG. 7D illustrates the surgical bed with a rounded track from FIGS. 7A, 7B, 7C. Top view 717 provides a different perspective of the positioning of mechanical arms 704, 705, 706, 708 to form a virtual rail to guide an endoscopic device 716 into an anatomical lumen in the lower abdomen of patient 709 for a procedure such as ureteroscopy, hysteroscopy, or colonoscopy.

Figure 7E:
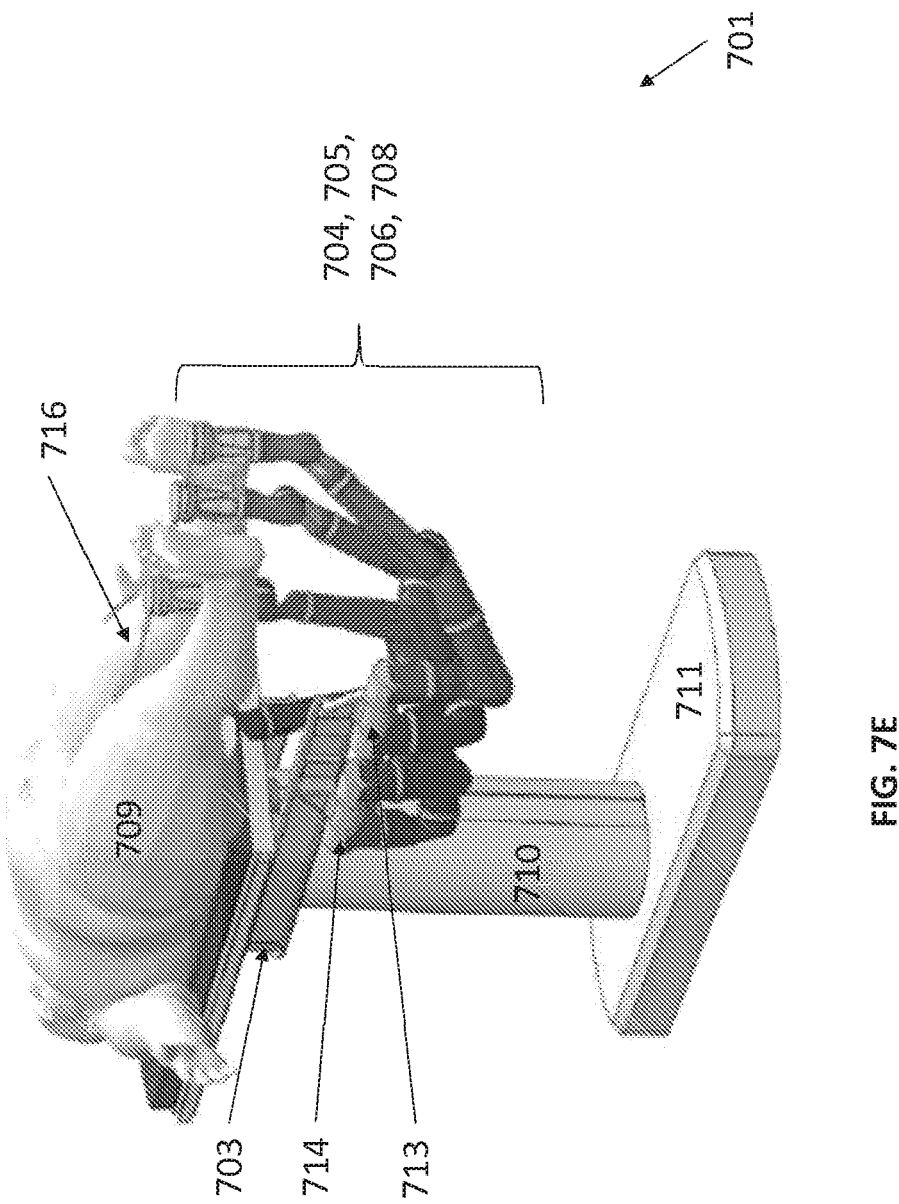
FIG. 7E illustrates the surgical bed with a rounded track from FIG. 7C.

FIG. 7E illustrates the surgical bed with a rounded track from FIG. 7C. Isometric view 718 provides an alternative positioning of mechanical arms 704, 705, 706, 708 to form a virtual rail to guide an endoscopic device 714 into an anatomical lumen in the lower abdomen of patient 709 for a procedure such as ureteroscopy, hysteroscopy, or colonoscopy. In view 717, the carriages 713 and 714 may be oriented below rail 703 to position mechanical arms 704, 705, 706, 708 such that the virtual rail is positioned lower than shown in FIGS. 7C and 7D.

Figure 7F:
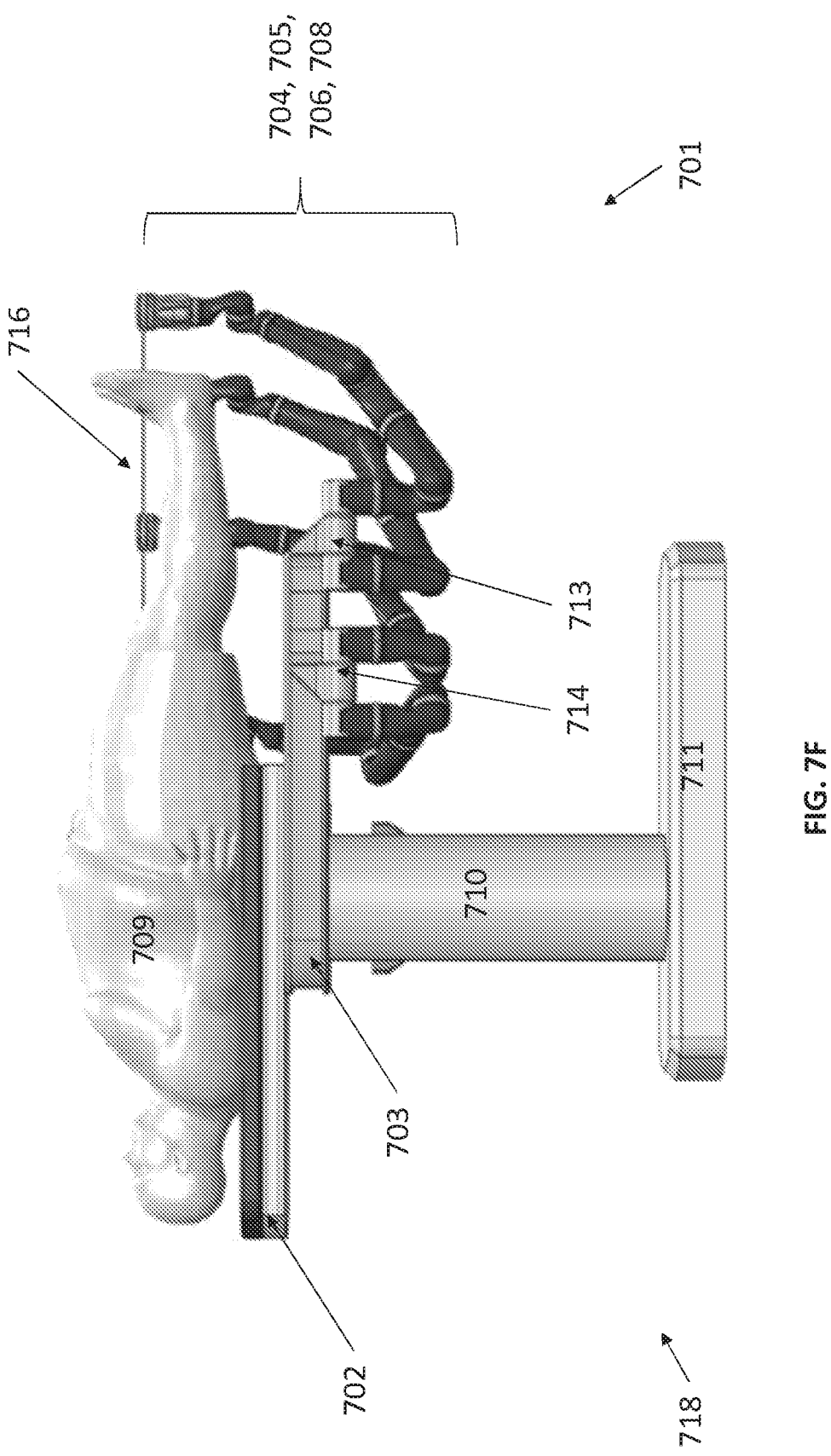
FIG. 7F illustrates the surgical bed with a rounded track from FIG. 7E.

FIG. 7F illustrates the surgical bed with a rounded track from FIG. 7E. Side view 719 provides a different perspective of the positioning of carriages 713 and 714 such that mechanical arms 704, 705, 706, 708 form a virtual rail to guide an endoscopic device 716 into an anatomical lumen in the lower abdomen of patient 709 for a procedure such as ureteroscopy, hysteroscopy, or colonoscopy.

Figure 7G:
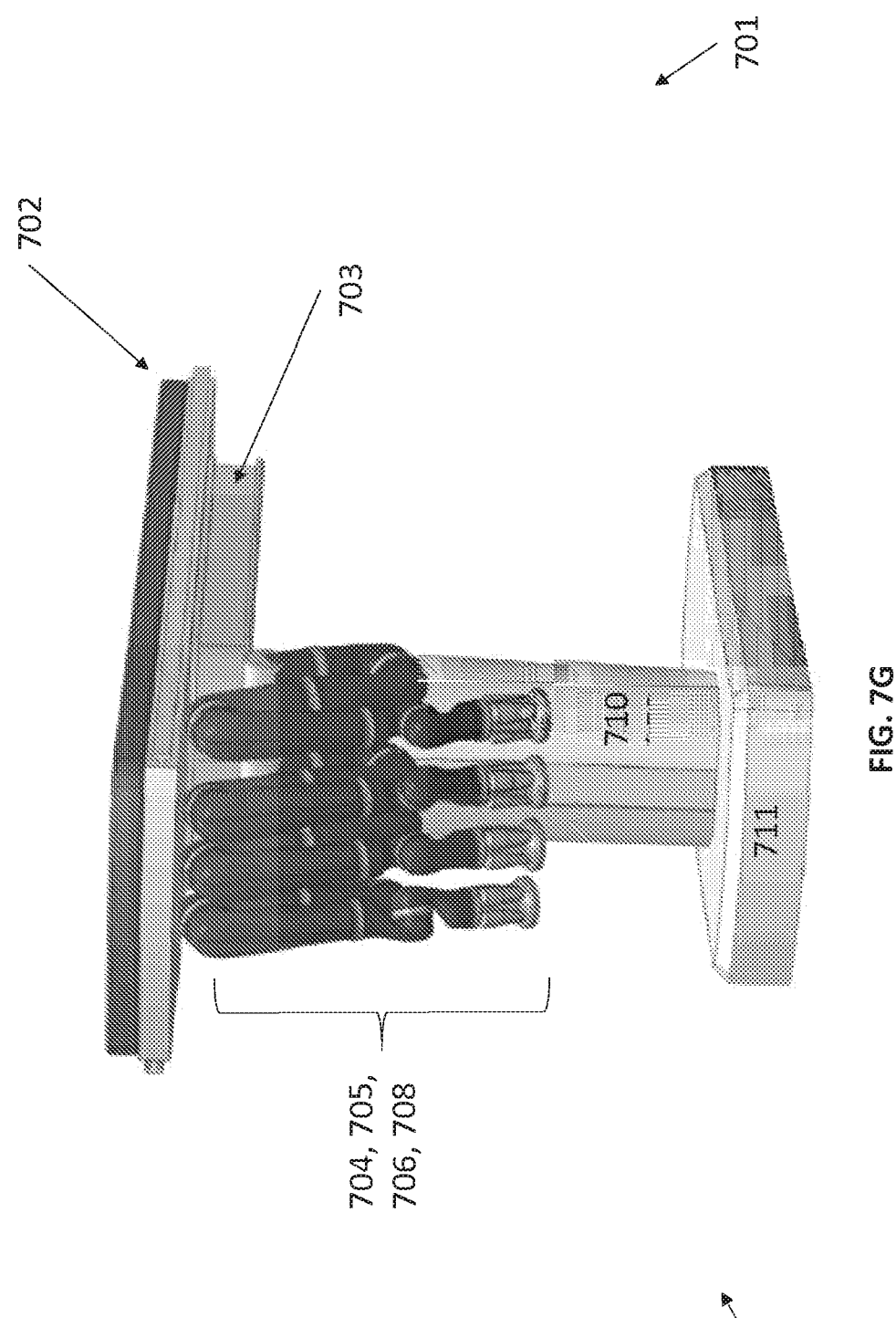
FIG. 7G illustrates the surgical bed with a rounded track from FIGS. 7A-7F.

FIG. 7G illustrates the surgical bed with a rounded track from FIGS. 7A-7F. View 719 shows stowage of mechanical arms 704, 705, 706, 708 through positioning of carriages 713 and 714 together along rail 703 under surgical bed 702.

Figure 8A:
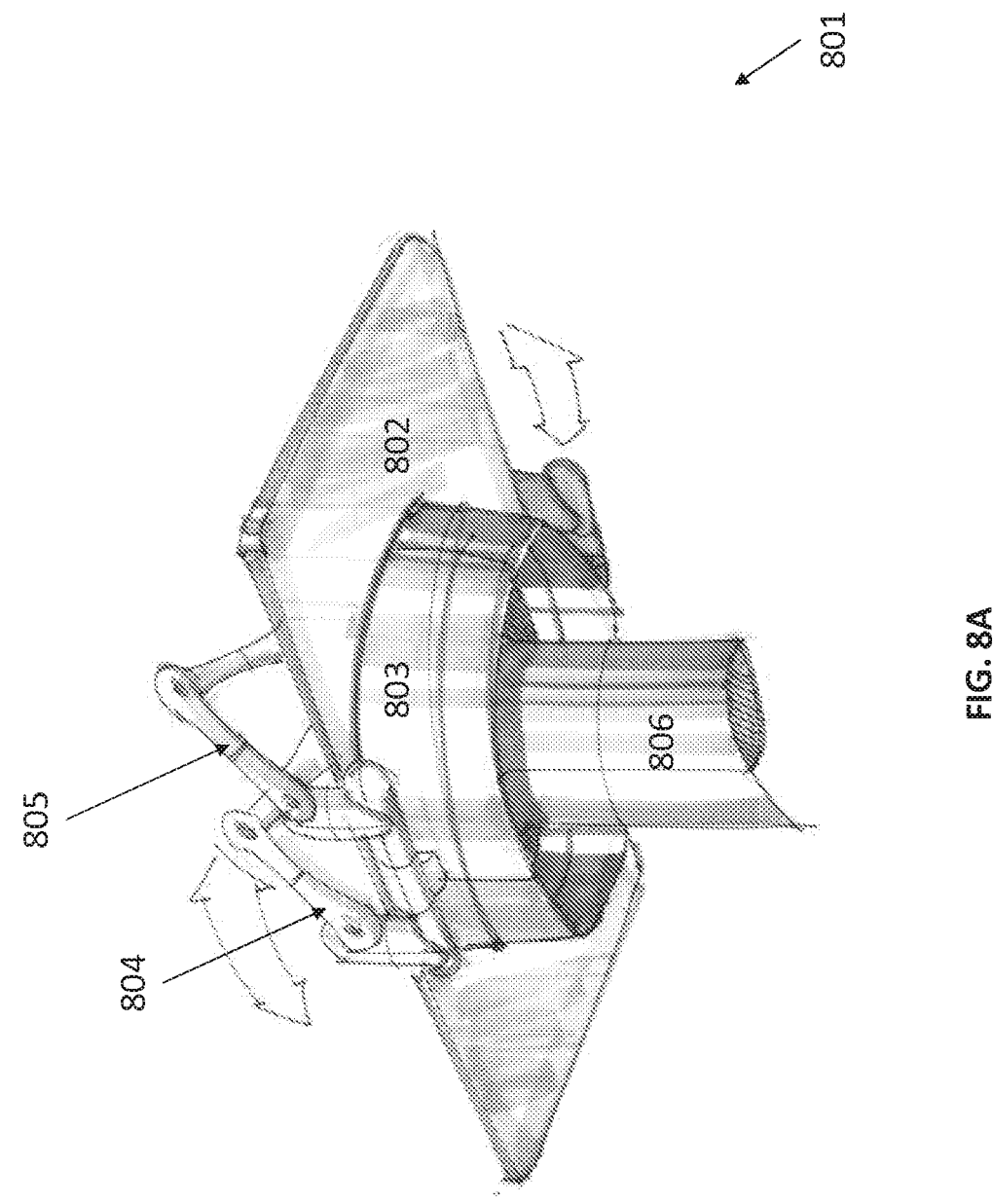
FIGS. 8A and 8B illustrate a surgical bed with a rounded track for robotic arms underneath the edge of the bed, consistent with an embodiment of the present invention.
Figure 8B:
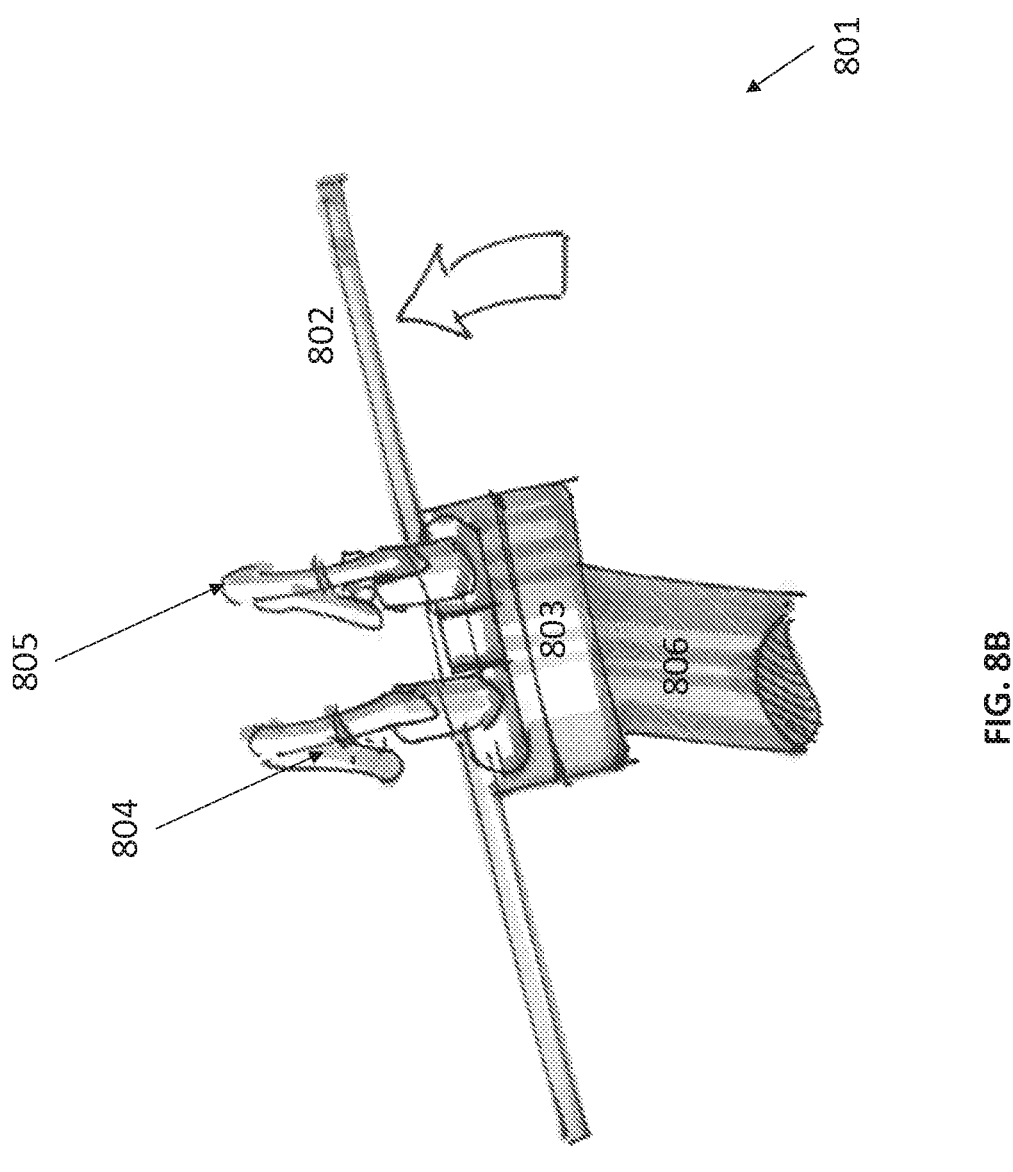

FIGS. 8A and 8B illustrate a surgical bed with a rounded track for robotic arms underneath the edge of the bed, consistent with an embodiment of the present invention. As shown in the view 800, the system 801 comprises of a surgical bed 802, a rail 803 (or "track") for mechanical arms, such as 804, 805. The surgical bed 802 may be configured to translate horizontally to position a patient relative to the mechanical arms. As shown in view 807 from FIG. 8B, the surgical bed 802 may tilted on the support stand 806 to improve physician access to the patient.

Underneath the surgical bed 802, the rail 803 provides a structure to slidingly translate the mechanical arms 804, 805 to a desired location around the surgical bed 802. The rail 803, which may be referred to as a "track", and the mechanical arms 804, 805 may be slidingly translated along it in order to facilitate access for the arms. The rail 803 also provides allows for the conveyance and reception of power, controls, fluidics, aspiration to the mechanical arms.

The mechanical arms may be operatively coupled to the rail 803. The mechanical arms may also be robotic. The translation of the mechanical arms 804, 805 may be actuated cither manually or robotically. The mechanical arms 804, 805 may be coupled independently to the rail 803 or individually or in groups via a mechanical carriage that may slide around the rail 803. In addition to providing structural support to the mechanical arms 804, 805 the carriage may be used to convey and receive power, controls, fluidics, aspiration to and from the arms 804, 805 to the support base 806. The ability to translate the arms 804, 805 and translate the bed 802 allows for nearly unlimited access to different portions of the anatomy of a patient.

System 801 may also incorporate support stand 806 to house electronics, fluidics, pneumatics, and aspiration. The electronics may be used from control, localization, navigation of the arms 804, 805. Thus, as a robotically-driven platform, system 801 provides for a comprehensive surgical bed and tool solution that may be used to perform any number of procedures around a patient. The rail 803 on support stand 806 may also translate vertically, allowing for easier access to the patient and operative site. The support stand may also telescope.

As deployed in view 800, mechanical arms 804, 805 may be positioned to access the abdomen of a patient for laparoscopic procedures, using a variety of rigid or semi-rigid laparoscopic instruments.

The aforementioned embodiments of the present invention may be designed to interface with robotics instrument device manipulators, tools, hardware, and software such as those disclosed in the aforementioned patent applications that are incorporated by reference. For example, the embodiments in this specification may be configured to be driven by an instrument drive mechanism or an instrument device manipulator that is attached to the distal end of a robotic arm through a sterile interface, such as a drape. As part of a larger robotics system, robotic control signals may be communicated from a remotely-located user interface, down the robotic arm, and to the instrument device manipulator to control the instrument or tool.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Elements or components shown with any embodiment herein are exemplary for the specific embodiment and may be used on or in combination with other embodiments disclosed herein. While the invention is susceptible to various modifications and alternative forms, specific examples thereof have been shown in the drawings and are herein described in detail. The invention is not limited, however, to the particular forms or methods disclosed, but to the contrary, covers all modifications, equivalents and alternatives thereof.

What is claimed is:

1. A medical system comprising:
a base;
a stand coupled to the base;
a bed supported by the stand, the bed having a length and a width, the length being longer than the width, the bed having:
    a lower body portion that protrudes from a first side of the stand,
    an upper body portion that protrudes from a second side of the stand opposite the first side of the stand,
    a first lateral edge that extends along the length of the bed, and
    a second lateral edge that extends along the length of the bed opposite the first lateral edge;
a first robotic arm having a proximal end supported beneath the bed and a distal end configured to manipulate a first medical instrument;
a second robotic arm having a proximal end supported beneath the bed and a distal end configured to manipulate a second medical instrument; and
control electronics configured to;
    drive movement of the first robotic arm and the second robotic arm to a stowed configuration where the first robotic arm and the second robotic arm are both positioned on the second side of the stand and beneath the upper body portion of the bed, and
    drive movement of the first robotic arm and the second robotic arm to a deployed configuration where the first robotic arm is raised over the first lateral edge of the bed and the second robotic arm is raised over the second lateral edge of the bed to perform a medical procedure.

2. The medical system of claim 1, further comprising:
a third robotic arm having a proximal end supported beneath the bed and a distal end configured to manipulate a third medical instrument,
the control electronics being configured to:
    drive movement of the third robotic arm to a stowed configuration where the third robotic arm is positioned on the second side of the stand together with the first robotic arm and the second robotic arm beneath the upper body portion of the bed.

3. The medical system of claim 1,
the first robotic arm and the second robotic arm being positioned beside each other in a folded configuration when in the stowed configuration, and
the first robotic arm and the second robotic arm being positioned on opposing sides of the bed in an extended configuration when in the deployed configuration.

4. The medical system of claim 1, the control electronics being configured to drive movement of the bed to a tilted configuration where the bed is tilted relative to the stand, and where the first robotic arm and the second robotic arm are tilted together with the bed relative to the stand.

5. The medical system of claim 1, the control electronics being configured to drive translation of the bed vertically relative to the base.

6. The medical system of claim 1, the control electronics being configured to drive translation of the bed horizontally relative to the base.

7. The medical system of claim 1, the proximal end of the first robotic arm and the proximal end of the second robotic arm being attached to a rail beneath the bed.

8. The medical system of claim 1, the stand housing at least some of the control electronics for control of the first robotic arm and the second robotic arm.

9. A medical system comprising:

a base;

a stand coupled to the base;

a bed supported by the stand, the bed having a substantially rectangular shape defining a length and a width, the length being longer than the width, the bed having:

a first longitudinal portion that protrudes from a first side of the stand, the first longitudinal portion terminating at a first longitudinal edge, a second longitudinal portion that protrudes from a second side of the stand opposite the first side of the stand, the second longitudinal portion terminating at a second longitudinal edge opposite the first longitudinal edge, a first lateral portion that protrudes from a third side of the stand, the first lateral portion terminating at a first lateral edge, and a second lateral portion that protrudes from a fourth side of the stand opposite the third side of the stand, the second lateral portion terminating at a second lateral edge opposite the first lateral edge;

a first robotic arm having a proximal end supported beneath the bed and a distal end configured to manipulate a first medical instrument;

a second robotic arm having a proximal end supported beneath the bed and a distal end configured to manipulate a second medical instrument; and control electronics configured to:

drive movement of the first robotic arm and the second robotic arm to a stowed configuration where the first robotic arm and the second robotic arm are both positioned on the first side of the stand and beneath the first longitudinal portion of the bed, and drive movement of the first robotic arm and the second robotic arm to a deployed configuration where the first robotic arm is raised over the first lateral edge of the bed and the second robotic arm is raised over the second lateral edge of the bed to perform a medical procedure.

10. The medical system of claim 9, further comprising:

a third robotic arm having a proximal end supported beneath the bed and a distal end configured to manipulate a third medical instrument, the control electronics being configured to:

drive movement of the third robotic arm to a stowed configuration where the third robotic arm is positioned on the second side of the stand together with the first robotic arm and the second robotic arm beneath the first longitudinal portion of the bed.

11. The medical system of claim 9, the first robotic arm and the second robotic arm being positioned beside each other in a folded configuration when in the stowed configuration, and the first robotic arm and the second robotic arm being positioned on opposing sides of the bed in an extended configuration when in the deployed configuration.

12. The medical system of claim 9, the control electronics being configured to drive movement of the bed to a tilted configuration where the bed is tilted relative to the stand, and where the first robotic arm and the second robotic arm are tilted together with the bed relative to the stand.

13. The medical system of claim 9, the control electronics being configured to drive translation of the bed vertically and horizontally relative to the base.

14. The medical system of claim 9, the proximal end of the first robotic arm and the proximal end of the second robotic arm being attached to a rail beneath the bed.

15. The medical system of claim 9, the stand housing at least some of the control electronics for control of the first robotic arm and the second robotic arm.

16. A method comprising:

supporting a center portion of a substantially rectangular surgical bed with a stand such that:

a first longitudinal portion of the surgical bed protrudes from a first side of the stand in a first longitudinal direction, the first longitudinal portion of the surgical bed terminating at a first longitudinal edge of the surgical bed, a second longitudinal portion of the surgical bed protrudes from a second side of the stand opposite the first side of the stand in a second longitudinal direction opposite the first longitudinal direction, the second longitudinal portion of the surgical bed terminating at a second longitudinal edge of the surgical bed opposite the first longitudinal edge, a first lateral portion of the surgical bed protrudes from a third side of the stand in a first lateral direction, the first lateral portion of the surgical bed terminating at a first lateral edge of the surgical bed, and a second lateral portion of the surgical bed protrudes from a fourth side of the stand opposite the third side of the stand in a second lateral direction opposite the first lateral direction, the second lateral portion of the surgical bed terminating at a second lateral edge of the surgical bed opposite the first lateral edge;

raising a first robotic arm over the first lateral edge of the surgical bed to perform a medical procedure;

raising a second robotic arm over the second lateral edge of the surgical bed to perform the medical procedure; and stowing the first robotic arm and the second robotic arm beneath the first longitudinal portion of the surgical bed such that the first robotic arm and the second robotic arm are positioned on the first side of the stand.

17. The method of claim 16, further comprising:

raising a third robotic arm over the first lateral edge of the surgical bed to perform the medical procedure; and stowing the third robotic arm beneath the first longitudinal portion of the surgical bed such that the third robotic arm is positioned together with the first robotic arm and the second robotic arm on the first side of the stand.

18. The method of claim 16, the stowing of the first robotic arm and the second robotic arm comprising:

positioning the first robotic arm and the second robotic arm beside each other in a folded configuration.

19. The method of claim 16, further comprising:

tilting the surgical bed relative to the stand, and tilting the first robotic arm and the second robotic arm with the surgical bed relative to the stand.

20. The method of claim 16, further comprising housing electronics in the stand for control of the first robotic arm and the second robotic arm.

<center>* * * * *</center>